United States Patent
Nguyen et al.

(10) Patent No.: US 11,154,350 B2
(45) Date of Patent: Oct. 26, 2021

(54) ABLATION CATHETER HAVING ELECTRONIC DEVICE DISPOSED WITHIN A LUMEN

(71) Applicant: ST. JUDE MEDICAL, ATRIAL FIBRILLATION DIVISION, INC., St. Paul, MN (US)

(72) Inventors: Ron Phan Nguyen, Garden Grove, CA (US); Terry Sterrett, Huntington Beach, CA (US); Kevin Herrera, Irvine, CA (US)

(73) Assignee: ST. JUDE MEDICAL, ATRIAL FIBRILLATION DIVISION, INC., St. Paul, MN (US)

( * ) Notice: Subject to any disclaimer, the term of this patent is extended or adjusted under 35 U.S.C. 154(b) by 895 days.

(21) Appl. No.: 14/198,009

(22) Filed: Mar. 5, 2014

(65) Prior Publication Data

US 2014/0276788 A1 Sep. 18, 2014

Related U.S. Application Data

(60) Provisional application No. 61/778,605, filed on Mar. 13, 2013.

(51) Int. Cl.
| | |
|---|---|
| *A61B 18/14* | (2006.01) |
| *A61B 18/00* | (2006.01) |
| *A61B 90/00* | (2016.01) |

(52) U.S. Cl.
CPC .............. *A61B 18/1492* (2013.01); *A61B 2018/00357* (2013.01); *A61B 2018/00821* (2013.01); *A61B 2090/064* (2016.02); *A61B 2218/002* (2013.01); *Y10T 29/49002* (2015.01)

(58) Field of Classification Search
CPC ............ A61B 2018/00011; A61B 2018/00166
See application file for complete search history.

(56) References Cited

U.S. PATENT DOCUMENTS

| | | | | | |
|---|---|---|---|---|---|
| 4,325,374 | A | * | 4/1982 | Komiya | A61B 18/14 606/47 |
| 4,411,266 | A | * | 10/1983 | Cosman | A61B 18/14 600/549 |
| 5,431,649 | A | * | 7/1995 | Mulier | A61B 18/1477 600/374 |
| 5,688,267 | A | * | 11/1997 | Panescu | A61B 18/1492 606/31 |
| 5,788,692 | A | * | 8/1998 | Campbell | A61B 18/18 600/374 |
| 6,099,524 | A | * | 8/2000 | Lipson | A61B 5/0422 600/374 |
| 6,626,902 | B1 | * | 9/2003 | Kucharczyk | A61B 5/14503 606/34 |

(Continued)

*Primary Examiner* — Ronald Hupczey, Jr.
(74) *Attorney, Agent, or Firm* — Armstrong Teasdale LLP

(57) ABSTRACT

The present disclosure relates generally to catheter devices, including irrigated and non-irrigated ablation catheters. More specifically, this disclosure relates to irrigated ablation catheters including an irrigation lumen having at least one electronic device at least partially disposed therein. In many embodiments, the irrigation lumen further includes at least one sideport. In some embodiments, the electronic device has a distal end extending out of the irrigation lumen and into an electrode tip assembly. In some embodiments, a proximal end of the electronic device extends through the sideport in the irrigation lumen.

10 Claims, 22 Drawing Sheets

(56) References Cited

U.S. PATENT DOCUMENTS

| | | | |
|---|---|---|---|
| 6,638,275 B1 * | 10/2003 | McGaffigan | A61B 18/1477 606/41 |
| 7,204,833 B1 * | 4/2007 | Osorio | A61B 5/4094 606/21 |
| 7,591,816 B2 * | 9/2009 | Wang | A61B 18/1492 606/41 |
| 7,771,420 B2 * | 8/2010 | Butty | A61B 18/1492 606/41 |
| 8,052,684 B2 | 11/2011 | Wang et al. | |
| 8,187,267 B2 | 5/2012 | Pappone et al. | |
| 8,221,409 B2 | 7/2012 | Cao et al. | |
| 8,900,288 B2 * | 12/2014 | Chobotov | A61F 2/07 623/1.13 |
| 9,486,275 B2 * | 11/2016 | Harrison | A61B 18/1477 |
| 2010/0152731 A1 | 6/2010 | de la Rama et al. | |
| 2012/0029504 A1 | 2/2012 | Afonso et al. | |
| 2012/0172857 A1 * | 7/2012 | Harrison | A61B 18/1477 606/33 |

\* cited by examiner

ABLATION CATHETER HAVING ELECTRONIC DEVICE DISPOSED WITHIN A LUMEN

CROSS-REFERENCE TO RELATED APPLICATIONS

This application claims priority to provisional application Ser. No. 61/778,605, filed Mar. 13, 2013, the entire specification of which is incorporated herein.

BACKGROUND OF THE DISCLOSURE a. Field of the Disclosure

This disclosure relates generally to catheter devices, including irrigated and non-irrigated ablation catheters. More specifically, this disclosure relates to irrigated ablation catheters including an electronic device disposed in or near a tip thereof.

b. Background Art

Electrophysiology catheters are used for an ever-growing number of medical procedures. For example, catheters are used for diagnostic, therapeutic, and ablative procedures. Typically, the catheter is manipulated through a patient's vasculature and to the intended site, such as a site within the patient's cardiovascular system, such as the heart or renal artery.

A catheter typically carries one or more electrodes, which may be used for ablation, diagnosis, or the like. There are a number of methods used for ablation of desired areas, including for example, radiofrequency (RF) ablation. RF ablation is generally accomplished by transmission of radiofrequency energy to a desired target area through an electrode assembly to ablate tissue at the target site.

Because RF ablation may generate significant heat, which can result in protein denaturation, blood coagulation, excess tissue damage including steam pop, tissue charring, and the like, it may be desirable to monitor the temperature of the ablation assembly. It may also be desirable to include a mechanism to irrigate certain target areas with biocompatible fluids, such as saline solution. This irrigation may reduce or avoid excess, unwanted tissue damage, and blood coagulation and problems associated therewith. The desired irrigation can be accomplished using either open irrigation catheters, which delivers cooling solution from a holding tank through open orifices on the electrode, or closed irrigation catheters, which circulate a cooling fluid within the inner cavity of the electrode. Both types of irrigation catheters are known in the art.

The temperature of the ablation assembly may be monitored during a procedure using a thermocouple, which may sometimes be placed within the tip of one or more electrodes of the ablation assembly.

The foregoing discussion is intended only to illustrate the present field and should not be taken as a disavowal of claim scope.

BRIEF SUMMARY OF THE DISCLOSURE

In various embodiments ablation catheters are disclosed that include at least one electronic device disposed within a lumen, and specifically within an irrigation lumen. The electronic device extends out of a distal end of the lumen and into an electrode tip assembly. In many embodiments described herein, the ablation catheter is an irrigated ablation catheter that includes at least one irrigation lumen in fluid connection with an electrode tip assembly. At least one electronic device is disposed within the irrigation lumen such that at least a portion of the electronic device extends out of the distal end of the irrigation lumen and into the electrode tip assembly. The wiring component of the electronic device is generally contained within the irrigation lumen and extends out of the irrigation lumen near the proximal end through a sideport or other means as described herein, where it can be directed into the handle of the catheter, or otherwise. The sideport in the irrigation lumen is sealed such that irrigation fluid traveling through the irrigation lumen does not leak at the sideport. The irrigation lumen that includes the electronic device disposed therein is sized and configured to allow for a clinically significant irrigation solution flow rate and pressure.

Embodiments of the present disclosure include embodiments where a thermocouple is the electronic device and the thermocouple sensor ball extends out of the distal end of the irrigation lumen and into a counterbore located in the electrode tip assembly. The counterbore including the thermocouple ball is sealed with an adhesive to keep irrigation fluid from exiting the fluid delivery lumen and contacting the thermocouple. The wiring component of the thermocouple is disposed within the irrigation lumen and extends out of the irrigation lumen at a sideport near the proximal end of the lumen. The sideport located within the irrigation lumen is sealed with a circumferential bead of adhesive or otherwise as described herein to prevent leakage of the irrigation solution.

In accordance with the present disclosure, the electronic device may suitably be any electronic device that can be designed and configured to be contained on the interior of a lumen, including an irrigation lumen. Some particular electronic assemblies include a thermocouple, a GPS sensor, a pressure sensor, a lab-on-a-chip device, and a transducer. Moreover, the ablation catheters described herein and including a lumen including at least one electronic device may be single lumen ablation catheters, or may be multi-lumen ablation catheters. Further, the ablation catheters may be irrigated ablation catheters, or non-irrigated ablation catheters.

The present disclosure is specifically directed to an irrigated ablation catheter comprising an electrode tip assembly, and irrigation lumen, and an electronic device. The irrigation lumen has a distal end and a proximal end. The electronic device has a distal end and a proximal end and is disposed at least partially within the irrigation lumen.

The present disclosure is further specifically directed to an irrigation lumen for an ablation catheter. The irrigation lumen comprises a tubular structure having a distal end, a proximal end, and a sideport. An electronic device having a distal end and a proximal end is disposed at least partially within the tubular structure. The distal end of the electronic device extends past the distal end of the tubular structure, and the proximal end of the electronic device extends through the sideport of the tubular structure.

The present disclosure is further specifically directed to an ablation catheter comprising an electrode tip assembly, a lumen, and an electronic device. The lumen has a distal end and a proximal end and is disposed at least partially in the electrode tip assembly. The electronic device has a distal end and a proximal end and is disposed at least partially within the lumen. The distal end of the electronic device extends past the distal end of the lumen and into the electrode tip assembly.

The present disclosure is further specifically directed to a method of manufacturing an irrigated ablation catheter. The method comprises: (i) introducing a sideport into an irrigation lumen having a distal end and a proximal end; (ii) introducing an electronic device having a distal end and a proximal end into the irrigation lumen, wherein the distal end of the electronic device extends through the distal end of the irrigation lumen and wherein the proximal end of the electronic device extends through the sideport in the irrigation lumen; and (iii) introducing the distal end of the irrigation lumen into an electrode tip assembly and connecting the irrigation lumen to the electrode tip assembly such that the distal end of the electronic device is positioned within the electrode tip assembly.

The foregoing and other aspects, features, details, utilities, and advantages of the present disclosure will be apparent from reading the following description and claims, and from reviewing the accompanying drawings.

DETAILED DESCRIPTION OF THE DISCLOSURE

Figure 1:
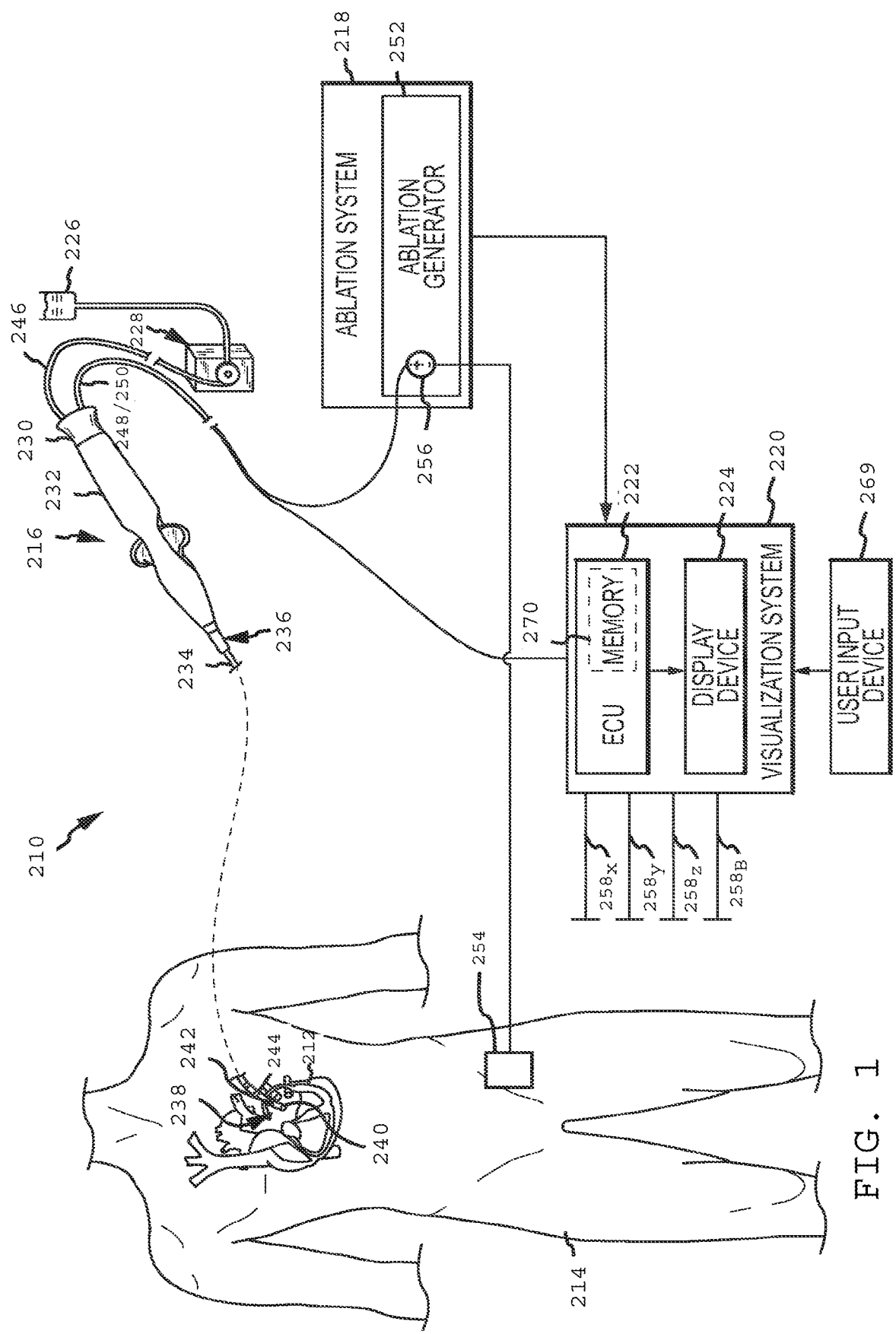
FIG. 1 is a diagrammatic view of a system for presenting information relating to lesion formation in tissue in accordance with the present teachings.

Because the amount of space within the electrode tip, as well as in the other components of the ablation assembly, is generally limited, in some cases an electronic device, such as a thermocouple for temperature monitoring, has been introduced into an electrode tip assembly of a catheter by shaping the thermocouple within the electrode tip such that the thermocouple ball sensor is positioned into the electrode tip counterbore. This design can, however, in some circumstances, potentially result in damage to the dielectric portion of the thermocouple during the manufacturing procedure, which can potentially hinder accurate temperature measurements during an ablation procedure. Additionally, this methodology can in some cases result in the exact placement of the thermocouple within the electrode tip being potentially variable and inconsistent, which can also hinder accurate temperature measurements.

Accordingly, a need exists for improved ablation catheters that can accommodate electronic devices, such as thermocouples, in a manner that decreases the potential for damage to the electronic devices during manufacture and use. Additionally, it would be beneficial if the new ablation catheters had improved consistency with regard to the placement of the electronic devices within the ablation catheter. Moreover, it would be desirable if the electronic devices could be incorporated into the ablation catheter in such a way that the electronic device occupied a reduced amount of space within the electrode tip.

In various embodiments, the present disclosure relates to ablation catheters suitable for use in medical procedures where ablation of tissue is required. In at least one embodiment, the ablation catheter includes at least one electronic device, such as a thermocouple, GPS sensor, and the like, that is disposed inside of a lumen, such as an irrigation lumen. A distal end of the electronic device may extend into an electrode tip assembly and a proximal end of the device may extend out of the lumen through a sideport or other exit means. Related methods of manufacturing and using such ablation catheters are also disclosed.

The present disclosure utilizes the space interior of a lumen to place electronic devices (including the wiring component of the electronic device) and thus increases the amount of free space available within the ablation catheter for other components. The electronic device disposed in the lumen may be wired through the interior of the lumen to an exit point and then into the catheter handle, for example. The present disclosure allows for the consistent, stable placement of an electronic device within an electrode tip assembly during manufacturing processes without significant potential of damaging the electronic device. Although described primarily herein in combination with an irrigated ablation catheter including an irrigation lumen in which a desired electronic device is disposed, the present disclosure also contemplates a non-irrigated ablation catheter that includes at least one lumen in which a desired electronic device is disposed. Additionally, the present disclosure contemplates multi-lumen catheters and multi-electrode catheters.

The disclosure and its various embodiments can now be better understood by turning to the following detailed description of numerous embodiments, which are presented as illustrative examples of the disclosure. It is expressly understood that the disclosure as set forth herein may be broader than the illustrated embodiments described below.

Referring now to the Figures, FIG. 1 illustrates one exemplary embodiment of system 210 for performing one or more diagnostic and/or therapeutic functions that includes components for presenting information representative of lesion formation in tissue 212 of body 214 during an ablation procedure performed thereon. In an exemplary embodiment, tissue 212 comprises heart or cardiac tissue within human body 214. It should be understood, however, that system 210 may find application in connection with the ablation of a variety of other tissues within human and non-human bodies.

Among other components, system 210 includes a medical device (such as, for example, catheter 216), ablation system 218, and system 220 for the visualization, navigation, and/or mapping of internal body structures. System 220 may include, for example and without limitation, an electronic control unit (ECU) 222, plurality of patch electrodes 258 ($258_x$, $258_y$, $258_z$, and $258_B$), display device 224 and user input device 269. Alternatively, ECU 222 and/or display 224 may be separate and distinct from, but electrically connected to and configured for communication with, system 220.

With continued reference to FIG. 1, catheter 216 is provided for examination, diagnosis, and/or treatment of internal body tissues such as tissue 212. In an exemplary embodiment, catheter 216 comprises an ablation catheter and, more particularly, an irrigated radio frequency (RF) ablation catheter. It should be understood, however, that catheter 216 is not limited to an irrigated catheter or an RF ablation catheter. Rather, in other embodiments, catheter 216 may comprise a non-irrigated catheter and/or other types of ablation catheters (e.g., cryoablation, ultrasound, etc.). In the exemplary embodiment wherein catheter 216 is an irrigated RF catheter, catheter 216 is connected to fluid source 226 providing a biocompatible fluid such as saline through pump 228 (which may comprise, for example, a fixed rate roller pump or variable volume syringe pump with a gravity feed supply from fluid source 226, as shown) for irrigation.

In an exemplary embodiment, catheter 216 is electrically connected to ablation system 218 to allow for the delivery of RF energy. Catheter 216 may include a cable connector or interface 230, handle 232, shaft 234 having a proximal end 236 and distal end 238 (as used herein, "proximal" refers to a direction toward the end of catheter 216 near the clinician, and "distal" refers to a direction away from the clinician and (generally) inside the body of a patient), and one or more electrodes 240 and 242 mounted in or on shaft 234 of catheter 216. In an exemplary embodiment, electrodes 240 and 242 are disposed at or near distal end 238 of shaft 234, with electrode 240 comprising an ablation electrode disposed at the extreme distal end 238 of shaft 234 (i.e., tip electrode 240), and electrode 242 comprising a positioning electrode used, for example, with the visualization, navigation, and mapping system 220. Catheter 216 may further include other conventional components such as, for example and without limitation, temperature sensor 244, additional electrodes (e.g., ring electrodes) and corresponding conductors or leads, or additional ablation elements, e.g., a high intensity focused ultrasound ablation element.

Connector 230 provides mechanical, fluid, and electrical connection(s) for cables 246, 248, and 250 extending from pump 228, ablation system 218, and visualization, navigation, and/or mapping system 220. Connector 230 is conventional in the art and is disposed at proximal end 236 of catheter 216.

Handle 232 provides a location for the clinician to hold catheter 216 and may further provide means for steering or guiding shaft 234 within body 214. For example, handle 232 may include means to change the length of a guidewire extending through catheter 216 to distal end 238 of shaft 234 to steer shaft 234. Handle 232 is also conventional in the art and it will be understood that the construction of handle 232 may vary. In another exemplary embodiment, catheter 216 may be robotically driven or controlled. Accordingly, rather than a clinician manipulating a handle to steer or guide catheter 216, and shaft 234 thereof, in particular, a robot is used to manipulate catheter 216.

Shaft 234 is an elongate, tubular, flexible member configured for movement within body 214. Shaft 234 supports, for example and without limitation, electrodes 240 and 242, associated conductors, and possibly additional electronics used for signal processing or conditioning. Shaft 234 may also permit transport, delivery and/or removal of fluids (including irrigation fluids, cryogenic ablation fluids, and bodily fluids), medicines, and/or surgical tools or instruments. Shaft 234 may be made from conventional materials such as polyurethane, and defines one or more lumens configured to house and/or transport at least electrical conductors, fluids, or surgical tools. Shaft 234 may be introduced into a blood vessel or other structure within body 214 through a conventional introducer. Shaft 234 may then be steered or guided through body 214 to a desired location such as tissue 212 with guidewires or other means known in the art.

With further reference to FIG. 1, ablation system 218 is comprised of, for example, ablation generator 252 and one or more ablation patch electrodes 254. Ablation generator 252 generates, delivers, and controls RF energy output by ablation catheter 216 and tip electrode 240 thereof, in particular. Generator 252 is conventional in the art and may comprises the commercially available unit sold under the model number IBI-1500T RF Cardiac Ablation Generator, available from Irvine Biomedical, Inc. In an exemplary embodiment, generator 252 includes RF ablation signal source 256 configured to generate an ablation signal that is output across a pair of source connectors: a positive polarity connector SOURCE (+), which may be electrically connected to tip electrode 240 of catheter 216; and a negative polarity connector SOURCE (−), which may be electrically connected to one or more of patch electrodes 254. It should be understood that the term connectors as used herein does not imply a particular type of physical interface mechanism, but is rather broadly contemplated to represent one or more electrical nodes. Source 256 is configured to generate a signal at a predetermined frequency in accordance with one or more user specified parameters (e.g., power, time, etc.) and under the control of various feedback sensing and control circuitry as is known in the art. Source 256 may generate a signal, for example, with a frequency of about 450 kHz or greater. Generator 252 may also monitor various parameters associated with the ablation procedure including, for example, impedance, the temperature at the distal tip of the catheter, applied ablation energy, and the position of the catheter, and provide feedback to the clinician or another component within system 210 regarding these parameters.

System 210 for performing one or more diagnostic and/or therapeutic functions that includes components for presenting information representative of lesion formation in tissue 212 of body 214 during an ablation procedure performed thereon as discussed generally herein is also described in U.S. Patent Publication No. 2012/0029504, published on Feb. 2, 2012, the entirety of which is hereby incorporated by reference.

Figure 2:
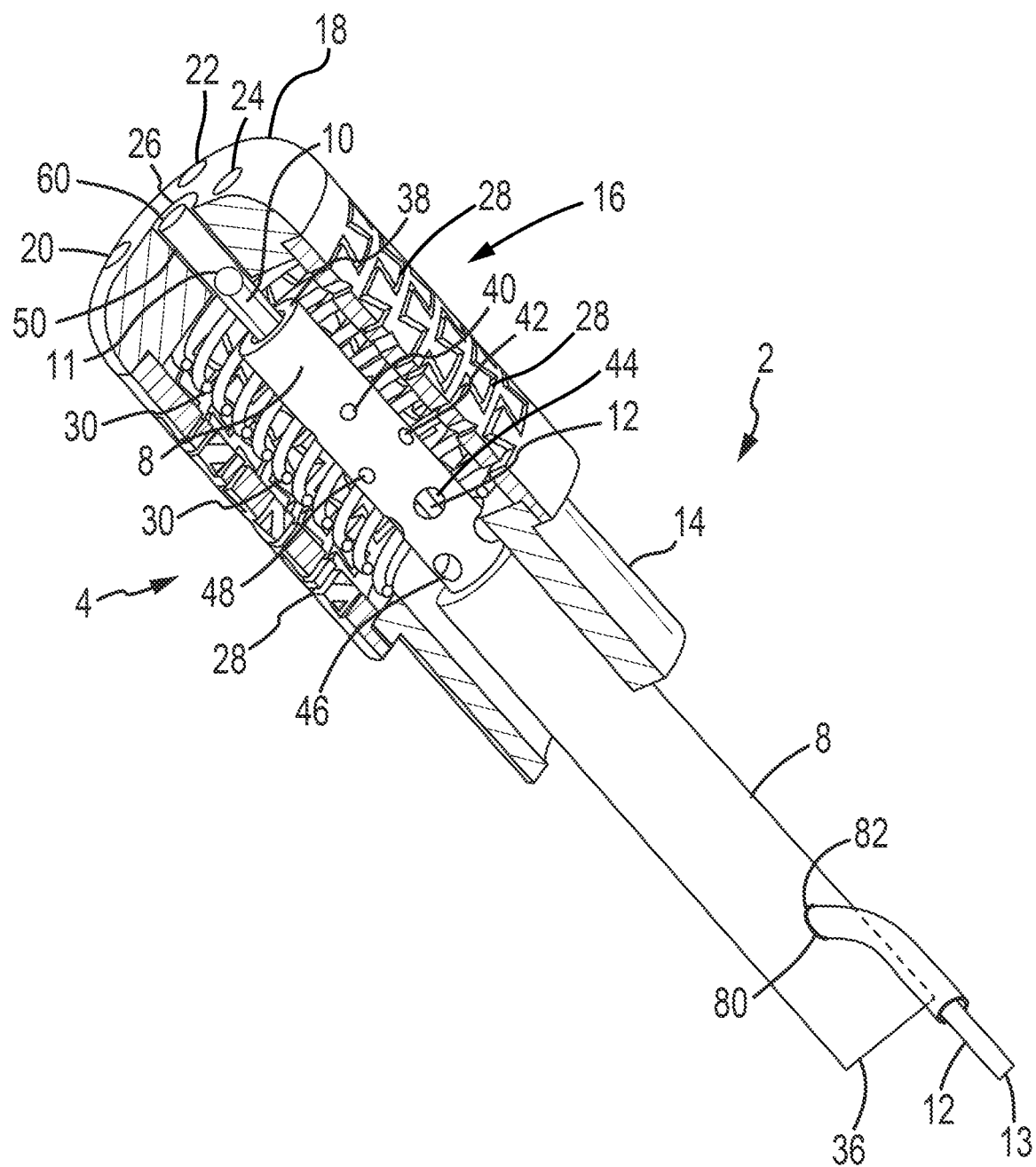
FIG. 2 depicts one embodiment of an ablation catheter of the present disclosure with portions cut away to reveal internal construction.

Turning now to FIG. 2, there is shown ablation catheter 2 of the present disclosure, with portions cut away to reveal internal construction. Ablation catheter 2 generally includes electrode tip assembly 4, irrigation lumen 8, electronic device 10, and electronic device wiring 12.

Electrode tip assembly 4 includes stem 14, generally cylindrical sidewall 16, dome tip 18, irrigation ports 20, 22, and 24, counterbore 26, annular surface channels 28 cut or formed into generally cylindrical sidewall 16, and biasing element 30. During an ablation procedure, electrode tip assembly 4 of ablation catheter 2 is navigated to a desired site in a body where a medical procedure, such as an ablation procedure, is to be done. In one embodiment, electrode tip assembly 4 may extend into the heart chamber of a patient. Such ablation procedures and related equipment are known to those of skill in the art.

Electrode tip assembly 4 of ablation catheter 2 is particularly suited for ablation procedures, wherein electrode tip assembly 4 is energized to deliver radio frequency (RF) waves at a site of an abnormal electrical pathway in the body. RF energy may therefore be applied to biological tissue in proximity to electrode tip assembly 4. Electrode tip assembly 4 may be fabricated from any suitable material, and is desirably machined from a platinum-iridium bar (90% platinum/10% iridium).

Electrode tip assembly 4 is illustrated in FIG. 2 as a flexible electrode tip assembly, although the present disclosure contemplates other non-flexible electrode tip assemblies that are known to those of ordinary skill in the art for use in the ablation catheters described herein. As shown in FIG. 2, electrode tip assembly 4 includes biasing element 30, which may be a spring coil in some embodiments. Biasing element 30 provides structural integrity to generally cylindrical sidewall 16 and resiliently maintains electrode tip assembly 4 in a predetermined configuration when no force is applied to electrode tip assembly. Biasing element 30 may be fabricated from a shape memory material that facilitates positioning electrode tip assembly 4.

As noted above, electrode tip assembly 4 also includes annular surface channels 28 cut or formed into generally cylindrical sidewall 16. Annular surface channels 28 are generally configured to channel an irrigation fluid (not shown) received from irrigation lumen 8 exterior electrode tip assembly 4. In the exemplary embodiment, annular surface channels 28 are structurally opened in a relaxed state and capable of opening more or less depending on the characteristics of a force vector imparted to electrode tip assembly 4. Annular surface channels 28 may be any suitable size and/or shape.

Ablation catheter 2 additionally includes irrigation lumen 8 having a proximal end 36 and a distal end 38. It should be understood that although FIG. 2 shows a single irrigation lumen 8, the disclosure herein contemplates that more than one irrigation lumen 8 can be implemented in a concentric or coaxial configuration or offset from the central axis of ablation catheter 2. Proximal end 36 may generally be in fluid communication with an irrigation fluid (not shown) that can travel through irrigation lumen 8 and into electrode tip assembly 4. Irrigation lumen 8 includes holes 40, 42, 44, 46, and 48, which disperse irrigation fluid (not shown) received from irrigation lumen 8 into electrode tip assembly 4 during an ablation procedure. As described in more detail below, irrigation lumen 8 may be a single piece irrigation lumen or may be a bonded multi-piece irrigation lumen comprising two, three or more pieces bonded together. Although not required, irrigation lumen 8 is generally tapered such that such that diameter of irrigation lumen 8 changes about its length as described herein. Additional details regarding a flexible electrode may be found in U.S. Pat. No. 8,187,267 and U.S. Patent Publication No. 2010/0152731, both of which are incorporated herein in their entirety.

As shown in FIG. 2, extending out of distal end 38 of irrigation lumen 8 and into electrode tip assembly 4 and into counterbore 26 is electronic device 10 having distal end 11 and proximal end 13. Electronic device 10 is contained within insulating element 50 having distal end 60, and includes electronic device wiring 12. Although generally illustrated as separate components herein, the term "electronic device" is intended to include electronic device 10 and electronic device wiring 12 attached thereto. Electronic device 10 and electronic device wiring 12 are disposed at least partially within irrigation lumen 8 in ablation catheter 2. Electronic device wiring 12 extends through irrigation lumen 8 via sideport 80 where it can be connected into a catheter handle (not shown) or to another connection point.

Although FIG. 2 illustrates a single electronic device 10 disposed within irrigation lumen 8 and extending into counterbore 26 of electrode tip assembly 4, the present disclosure contemplates that more than one electronic device may be disposed within irrigation lumen 8 and extend into counterbore 26 of electrode tip assembly 4. So long as a desired flow rate and pressure for an irrigation fluid can be maintained, there is no limit on the number of electronic devices that may be disposed in irrigation lumen 8. The present disclosure also contemplates an ablation catheter having one or more electronic devices disposed within in irrigation lumen 8 and extending into counterbore 26 along with one or more other electronic devices extending into electrode tip assembly 4 but not disposed within irrigation lumen 8. Also, irrigation lumen 8 may include more than one sideport, including 2, 3, 4, or more sideports.

Electronic device 10, including electronic device wiring 12, that is disposed at least partially within irrigation lumen 8 as shown in FIG. 2, may be any electronic device that can be suitably sized and configured to be introduced into and fed or threaded through irrigation lumen 8 during manufacturing of ablation catheter 2 as described below. Although generally illustrated and discussed herein as a thermocouple electronic device, electronic device 10 as described herein can be any number of specifically useful electronic devices within ablation catheter 2. Some non-limiting examples of suitable electronic assemblies for inclusion in ablation catheter 2 described herein, in addition to a thermocouple, include a pressure monitor, a global positioning system (GPS) sensor (such as a MediGuide™ sensor), a lab-on-a-chip device, a transducer, and combinations thereof. Additionally, although many of the illustrated and described embodiments herein include a single electronic device disposed with a lumen, such as an irrigation lumen, as noted above it is within the scope of the present disclosure to have more than one electronic device disposed within irrigation lumen 8.

Figure 3A:
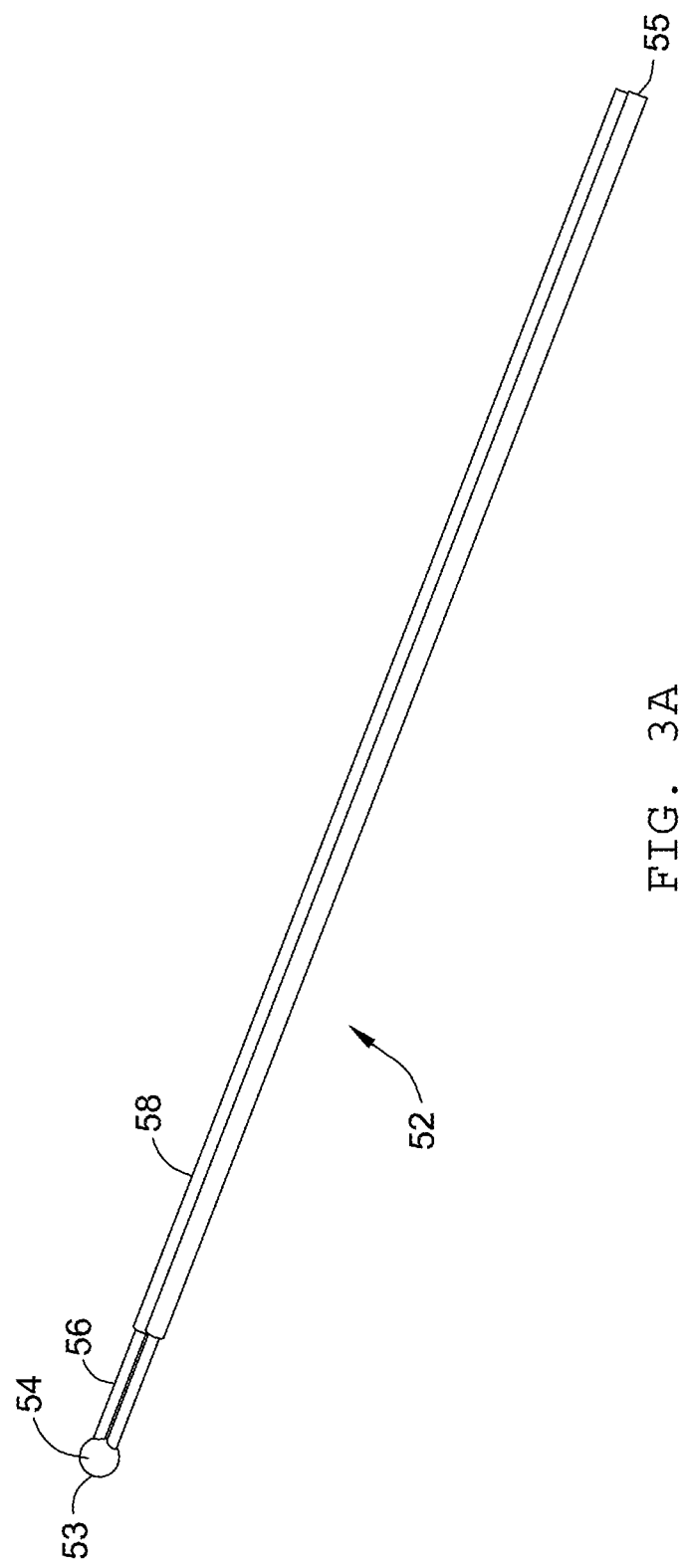
FIGS. 3A-3C depict a thermocouple as an exemplary electronic device and its assembly for use in the ablation catheter of FIG. 2.
Figure 3B:
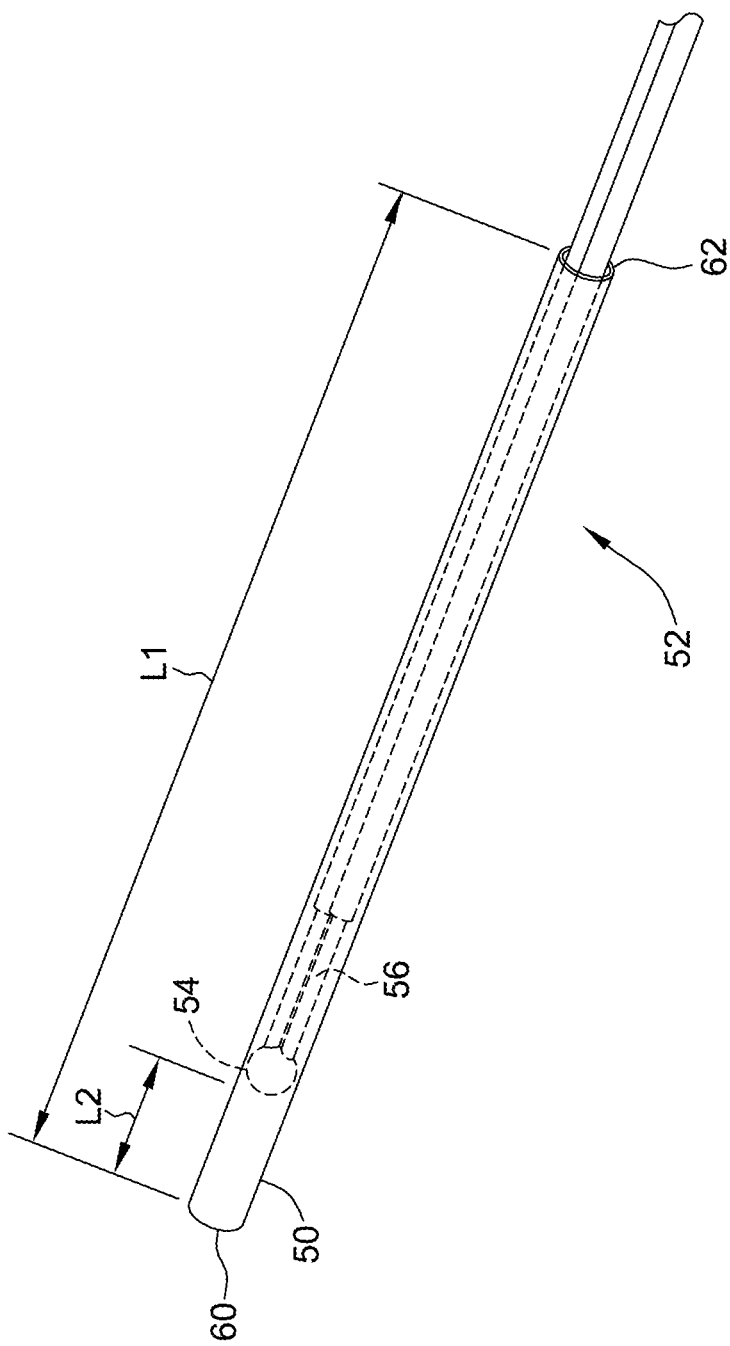
Figure 3C:
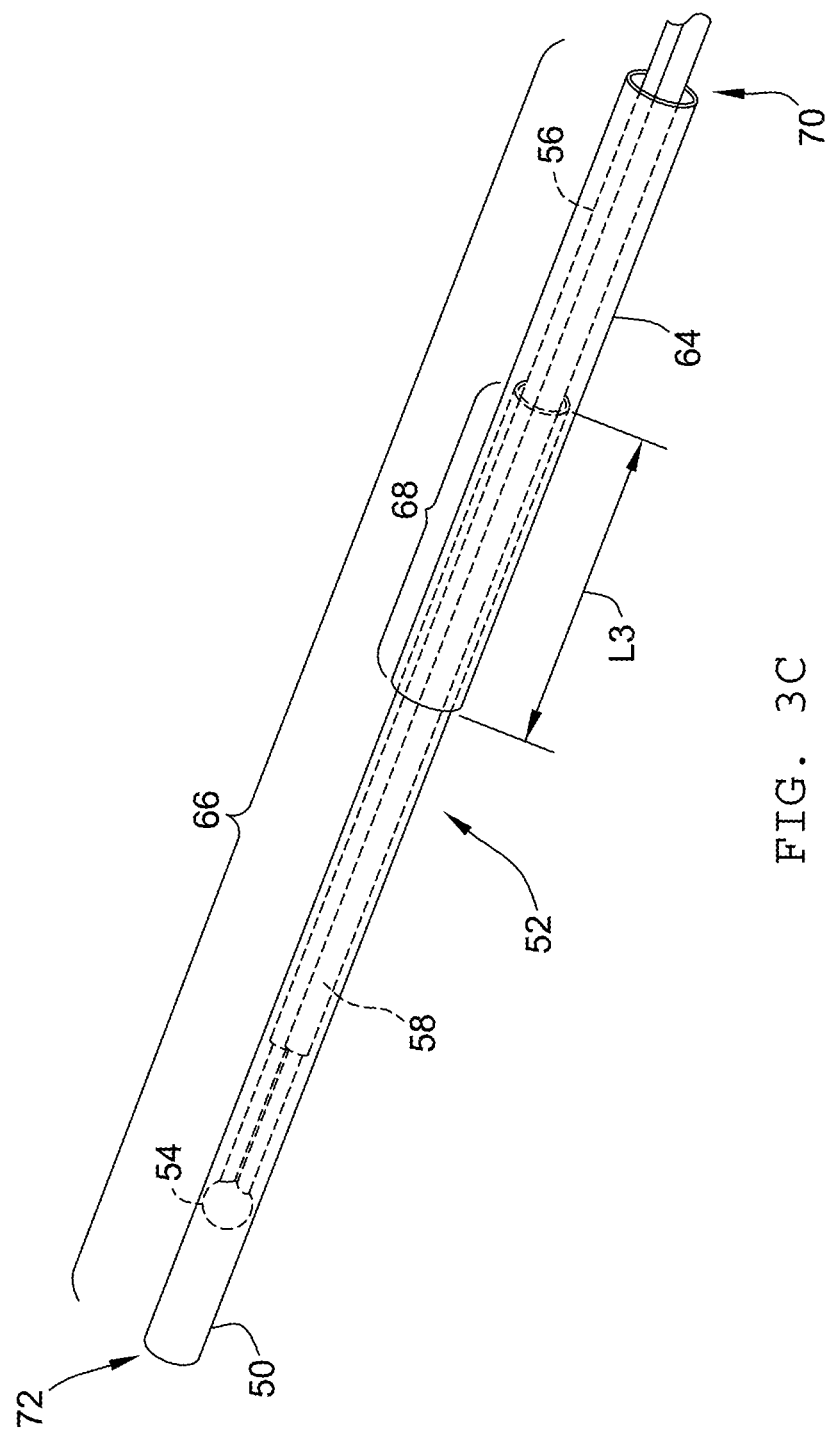

Turning now to the manufacturing of ablation catheter 2 including electronic device 10 disposed within irrigation lumen 8 as shown in FIG. 2, electronic device 10, including electronic device wiring 12, may suitably be fabricated and prepared for incorporation into ablation catheter 2. FIGS. 3A-3C illustrate the preparation of a thermocouple (exemplary electronic device 10) for insertion into irrigation lumen 8 for use in ablation catheter 2. Although FIGS. 3A-3C illustrate a thermocouple as electronic device 10, as noted herein the thermocouple could be replaced with any suitable electronic device described above.

FIG. 3A shows thermocouple 52 having distal end 53 and proximal end 55 and including thermocouple sensor 54, thermocouple wiring 56, and thermocouple wiring cover 58. In preparation of thermocouple 52 for use as electronic device 10 in ablation catheter 2 (as shown in FIG. 2), thermocouple 52 including thermocouple sensor 54 and thermocouple wiring 56 is introduced into insulating element 50 (also shown in FIG. 2) having length L1, distal end 60 and proximal end 62, as shown in FIG. 3B. Generally, insulating element 50 is slid over thermocouple wiring 56 toward thermocouple sensor 54.

Insulating element 50 may be constructed of any material suitable for providing the desired insulating and dielectric properties to thermocouple 52, but is desirably constructed of a polyimide material sized and configured to allow the insertion of thermocouple 52 therein. Insulating element 50 may have any length L1 suitable for the desired thermocouple 52, but is desirably from about 10 millimeters to about 30 millimeters, including about 20 millimeters in length. Insulating element 50 will desirably extend past thermocouple sensor 54 by length L2 to ensure proper insulating and dielectric properties for thermocouple 52. Length L2 may be any suitable length to achieve the desired insulating and dielectric properties, but is desirably from about 0.1 millimeters to about 1 millimeter, including about 0.35 millimeters. Insulating element 50 will have a suitable outside diameter and inside diameter to accommodate thermocouple 52, and may for example have an outside diameter of about 0.0095 inches (0.2413 millimeters) and an inside diameter of about 0.008 inches (0.2032 millimeters).

Once thermocouple 52 is properly positioned within insulating element 50, thermocouple 52 is stabilized in insulating element 50 using an adhesive or epoxy (not shown), such as a thermally conductive adhesive or thermally conductive epoxy. One suitable adhesive is OMEGABOND™ (Omega Engineering, Stamford, Conn.). Other suitable adhesives or epoxies are known to those of skill in the art and are suitable for use in the present disclosure. The adhesive or epoxy fills in any open space in insulating element 50 through capillary action and stabilizes thermocouple 52 therein while providing thermally conductive properties.

Referring now to FIG. 3C, once thermocouple 52, including thermocouple sensor 54 and thermocouple wiring 56, has been positioned within insulating element 50, and stabilized with the adhesive (not shown), extension tube 64 is attached to insulating element 50 to produce electronic device assembly 66 to cover thermocouple wiring cover 58 and provide overlap region 68 having length L3 such that electronic device assembly 66 may be threaded through irrigation lumen 8 (as shown in FIG. 2) as described below. Electronic device assembly 66 has proximal end 70 and distal end 72. Extension tube 64 has a larger outside diameter than insulating element 50 such that extension tube 64 can be fit around insulating element 50 and positioned appropriately. In one embodiment, extension tube 64 has an outside diameter of about 0.012 inches (0.3048 millimeters) and an inside diameter of about 0.10 inches (0.2540 millimeters). Extension tube 64 may be constructed of the same material or different material than insulating element 50, and may desirably be constructed of a polyimide material.

Extension tube 64 overlaps insulating element 50 to the extent necessary to ensure a strong, tight fit that can withstand flexible movements. Although any amount of overlap that accomplishes the intended function is within the scope of the present disclosure, desirably L3 has a length of at least 0.5 millimeter, desirably at least 1.0 millimeter, and desirably at least 2.0 millimeters. Once extension tube 64 is properly positioned around insulating element 50 and the desired length L3 has been obtained, extension tube 64 is secured to insulating element 50 using a suitable adhesive material or epoxy material as described above. Although illustrated as two separate pieces, it will be recognized by one of skill in the art that electronic device assembly 66 could be constructed of a single piece of material. For manufacturing purposes, however, it may be desirable to use two separate pieces as first threading electronic device 10 through a shorter piece and then attaching the shorter piece to a longer piece may be desirable as threading electronic device 10 through a single, longer piece may be more challenging and time consuming.

Irrigation lumen 8 may be prepared by first selecting the desired material and length for irrigation lumen 8. Irrigation lumen 8 may be fabricated from a suitable biocompatible material including at least one of a polyimide material, a polyether block amide material, a silicone material, a polyurethane material, or a combination thereof. Polyimide materials are generally desirable. As noted above, irrigation lumen 8 may be fabricated from a single piece of material or, as illustrated herein, may be desirably fabricated from two or more pieces of material that are suitably joined together using, for example, a suitable adhesive or epoxy material. Irrigation lumen 8 as shown in FIG. 2 is constructed of multiple pieces of material joined together as discussed in more detail below. When irrigation lumen 8 is constructed of two or more pieces of material that are joined together, the pieces may be of the same or different materials. Additionally, in many embodiments, irrigation lumen 8 may include one or more pieces of material that are tapered such that the circumference of the material changes about its length.

The length of irrigation lumen 8 may be selected based on the requirements of the specific ablation catheter to be constructed. The length selected should be sufficient to allow irrigation lumen 8 to extend from electrode tip assembly 4 (as shown in FIG. 2) and into an irrigation solution (not shown). Typically, the length of irrigation lumen 8 may be from about 500 millimeters to about 2000 millimeters, including from about 1000 millimeters to about 1500 millimeters, including about 1350 millimeters. In one exemplary embodiment, irrigation lumen 8 has a length of about 1360 millimeters.

Figure 4:
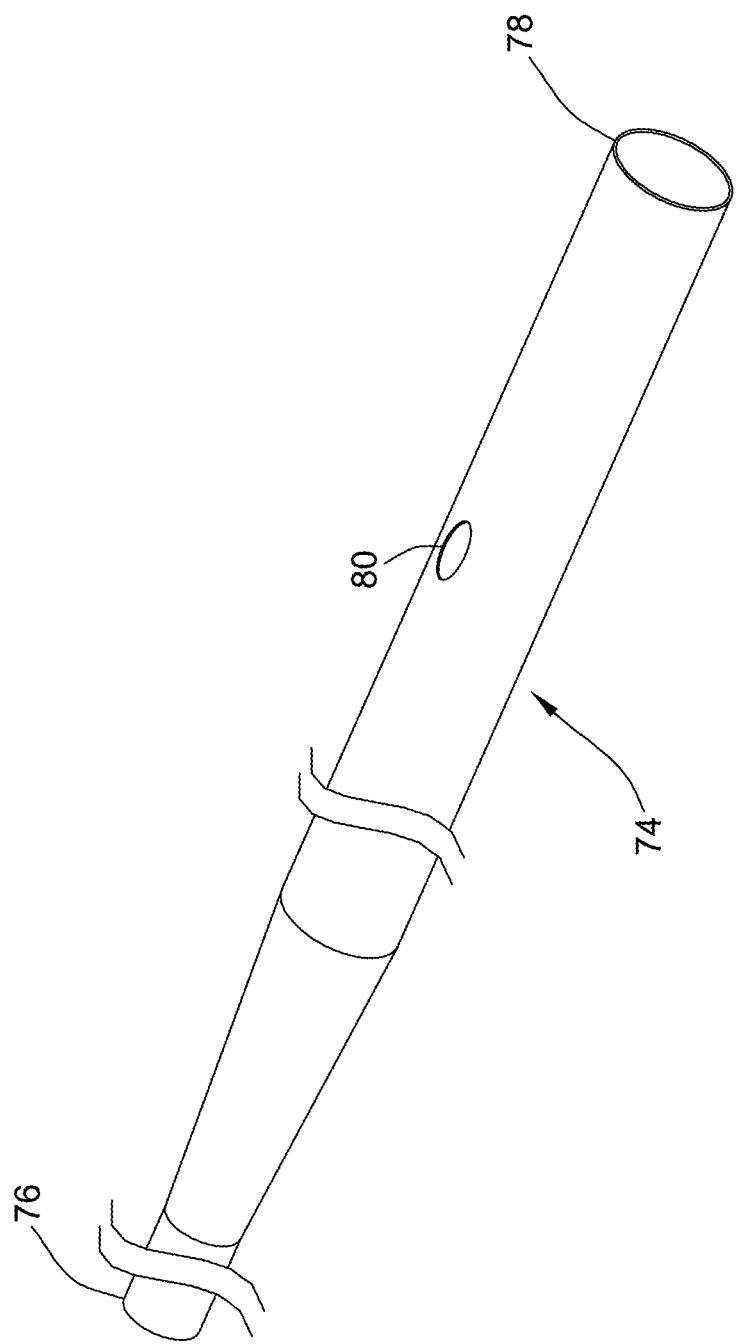
FIG. 4 depicts a first section of a lumen for use in an ablation catheter.

As shown in FIG. 4, once the desired material and length of irrigation lumen 8 is selected, construction of irrigation lumen 8 begins in one embodiment with introducing sideport 80 by laser drilling or other means into one wall of a suitable first lumen section 74 that is ultimately incorporated into irrigation lumen 8. When the material selected for irrigation lumen 8 is a polyimide material, the diameter of sideport 80 is selected to have a slight clearance with electronic device assembly 66 to minimize the potential for tearing and assist with fitting and providing a water tight bond, as described below. In one embodiment where a polyimide material is chosen to construct irrigation lumen 8, sideport 80 has a diameter that is from about 0.0002 inches (about 0.0051 millimeters) to about 0.0005 inches (about 0.0127 millimeters) larger than the outside diameter of electronic device assembly 66. When the material selected for irrigation lumen 8 is other than a polyimide material and is, for example, a polyurethane material, the diameter of sideport 80 is selected to have a slight interference fit with electronic device assembly 66 to assist with fitting and providing a water tight bond, as described below. When an interference fit is desired, sideport 80 has a diameter that is from about 0.0002 inches (about 0.0051 millimeters) to about 0.0005 inches (about 0.0127 millimeters) smaller than the outside diameter of electronic device assembly 66. A suitable diameter for sideport 80 in all embodiments may be, for example, about 0.0125 inches (about 0.3175 millimeters).

FIG. 4 shows first lumen section 74 having distal end 76, proximal end 78 and sideport 80. First lumen section 74 is suitably a tapered first lumen section (although in other embodiments first lumen section may not be tapered), that may, in one example, have an outside diameter of about 0.033 inches (about 0.8382 millimeters) and an inside diameter of about 0.032 inches (0.8128 millimeters) at proximal end 78 of first lumen section 74, with the outside diameter and inside diameter decreasing lengthwise toward distal end 76 as desired. Sideport 80 is desirably located near proximal end 78 of first lumen section 74, and allows for electronic device assembly 66 (as shown in FIG. 3C) to be inserted and routed therein as described more fully below. In one exemplary embodiment when irrigation lumen 8 has a length of about 1360 millimeters, sideport 80 is located about 60 millimeters from proximal end 36. Although illustrated in FIG. 4 as having a single sideport 80, first lumen section 74 may optionally have a second or even a third sideport in accordance with the present disclosure.

Figure 5:
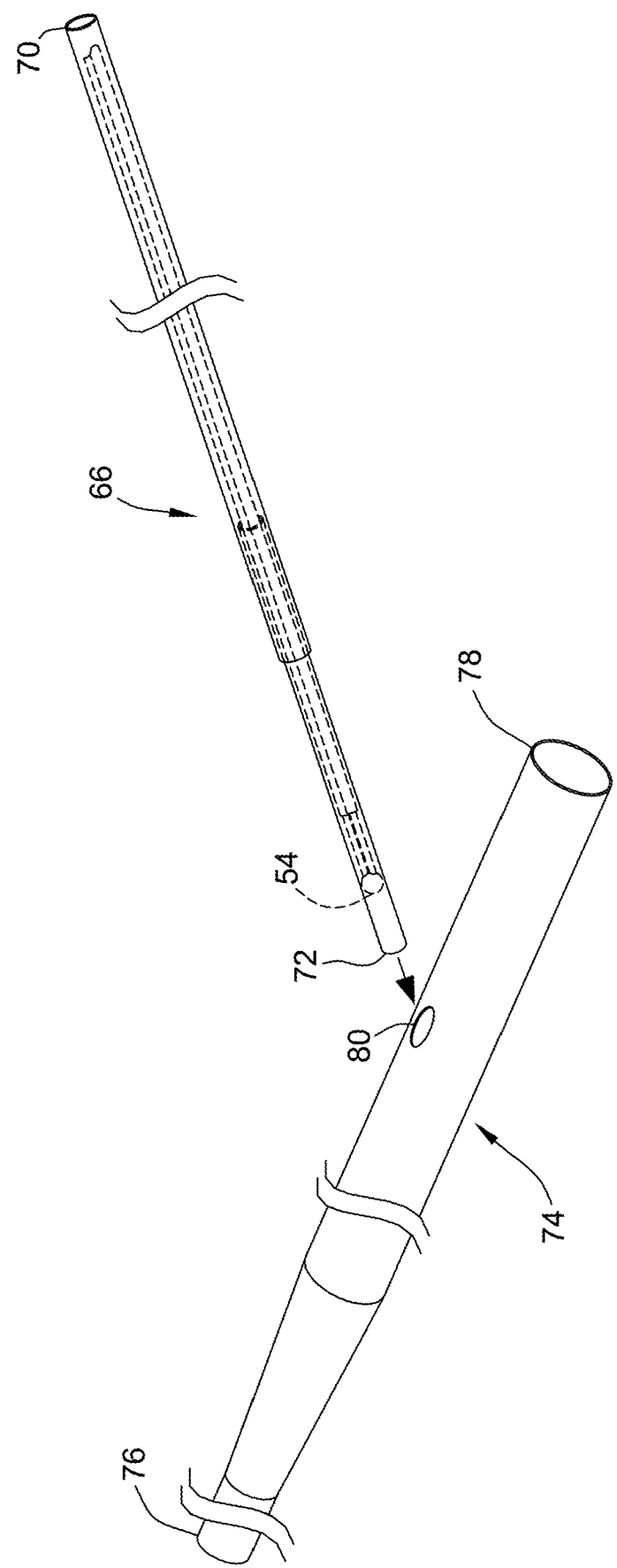
FIG. 5 depicts an electronic device being introduced into a first section of a lumen.
Figure 6:
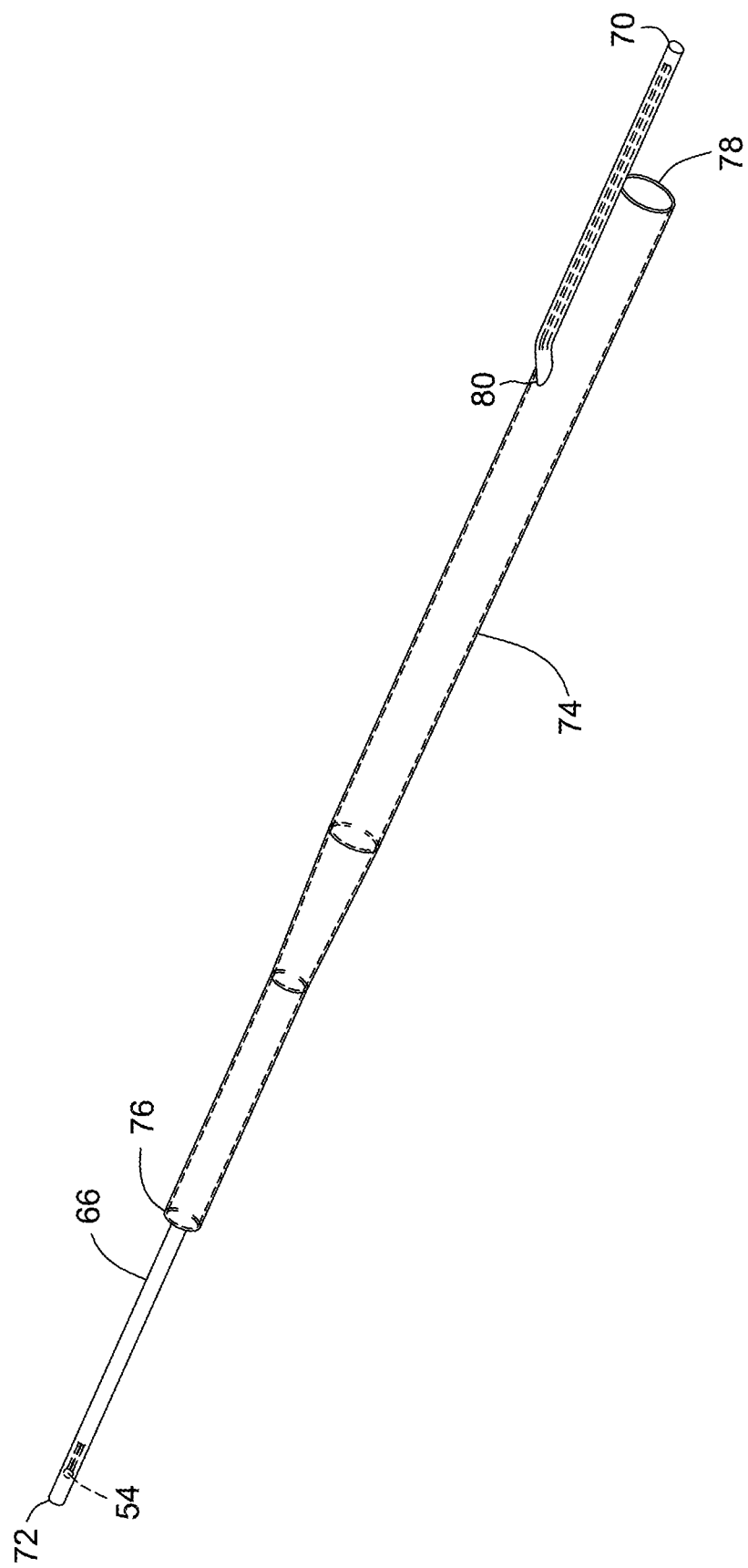
FIG. 6 depicts an electronic device positioned partially within a first section of a lumen and extending through a sideport.

Once sideport 80 has been introduced into first lumen section 74, electronic device assembly 66 may be inserted into first lumen section 74. As shown in FIGS. 5 and 6, in one embodiment, distal end 72 of electronic device assembly 66 is introduced into sideport 80 of first lumen section 74 near proximal end 78 and fed or threaded through the length of first lumen section 74 until distal end 72 of electronic device assembly 66 protrudes from distal end 76 of first lumen section 74. Sideport 80 allows electronic device assembly 66, which includes thermocouple sensor 54, to extend through first lumen section 74 and be routed to another portion of an ablation catheter (not shown), such as an ablation catheter handle (not shown).

Alternatively, in another embodiment, electronic device assembly 66 may be fed or threaded through first lumen section 74 by introducing proximal end 70 of electronic device assembly 66 into distal end 76 of first lumen section 74 and threading proximal end 70 through the length of first lumen section 74 and out of sideport 80 toward proximal end 78 of first lumen section 74.

Figure 7:
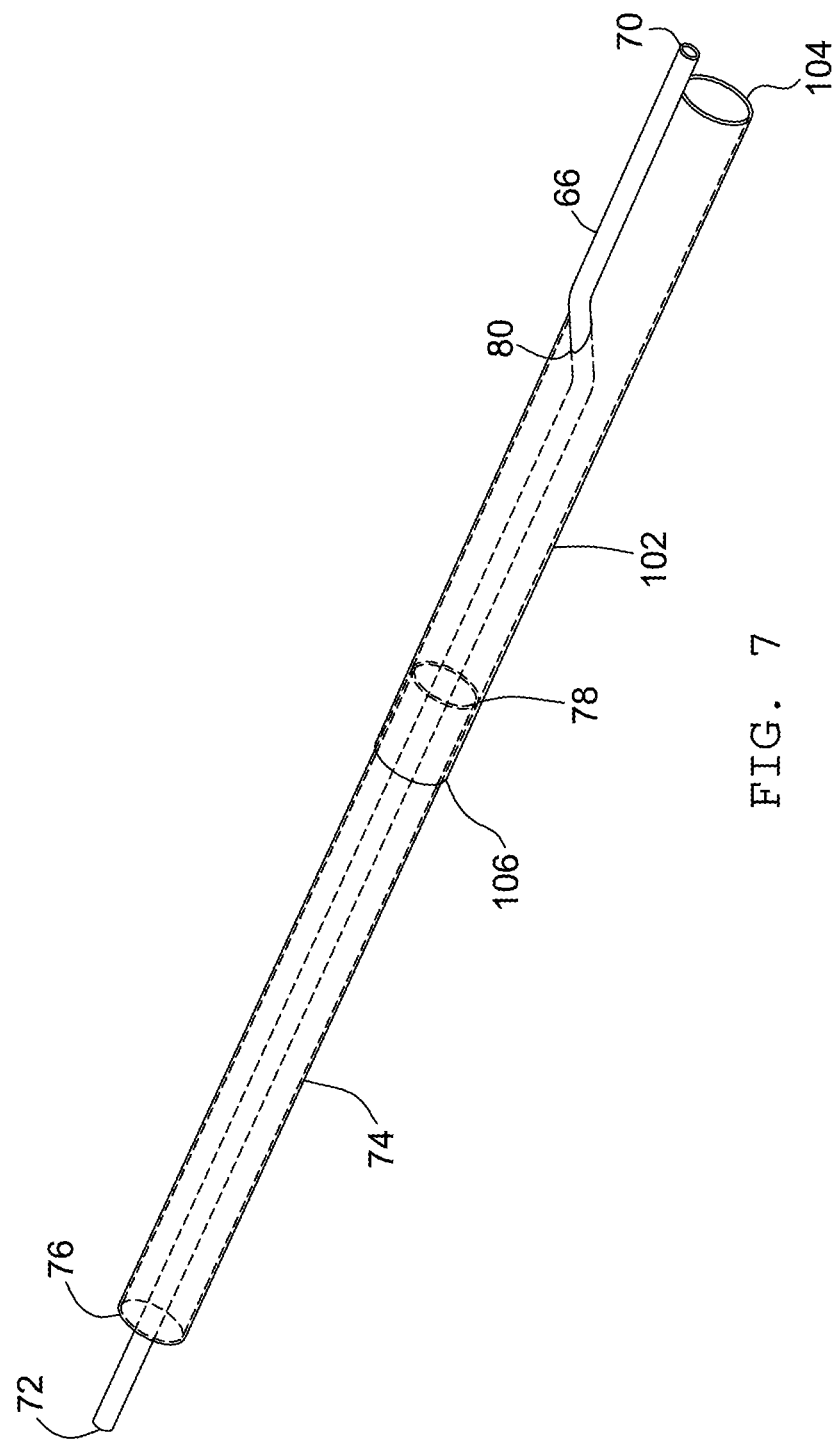
FIG. 7 depicts one embodiment for introducing an electronic device into a lumen.

Alternatively, in another embodiment as shown in FIG. 7, electronic device assembly 66 may be first fed or threaded through short assembly tube 102 and short assembly tube 102 subsequently connected to first lumen section 74. Short assembly tube 102 has proximal end 104 and distal end 106, and is significantly shorter the first lumen section 74 and may be, for example, between about 25 millimeters and about 75 millimeters in length, including about 50 millimeters in length. Because of the short length of short assembly tube 102, threading electronic device assembly 66 therethrough is generally easier and can, in some embodiments, result in less damage to electronic device assembly 66 and a time savings. Electronic device assembly 66 may be fed or threaded into short assembly tube 102 by either inserting distal end 72 of electronic device assembly 66 into sideport 80 and feeding electronic device assembly 66 through to distal end 106 of short assembly tube 102, or proximal end 70 of electronic device assembly 66 may be inserted into distal end 106 of short assembly tube 102 and fed through sideport 80.

Referring again to FIG. 7, once electronic device assembly 66 has been introduced into short assembly tube 102, distal end 106 of short assembly tube 102 is fitted over proximal end 78 of first lumen section 74 and electronic device assembly 66 is fed through first lumen section 74 until it protrudes from distal end 76 of first lumen section 74. Short assembly tube 102 overlaps first lumen section 74 in an amount sufficient to assure a strong connection and may overlap an amount of from about 1 millimeter to about 5 millimeters, including about 3 millimeters. Short assembly tube 102 and electronic device assembly 66 are bonded together using a suitable adhesive or epoxy as described herein. Short assembly tube 102 has an outside diameter larger than that of first lumen section 74 to allow short assembly tube 102 to be fit over the outside diameter of first lumen section 74. Suitably, in some embodiments, short assembly tube 102 may have an outside diameter of about 0.039 inches (about 0.9906 millimeters) and an inside diameter of about 0.036 inches (about 0.9144 millimeters). Short assembly tube 102 may be constructed from the same material as first lumen section 74, or may be constructed from a different material.

In many embodiments described herein, first lumen section 74 is part of irrigation lumen 8, which carries an irrigation fluid (not shown in the Figures) to electrode tip assembly 4 (as shown in FIG. 2) during an ablation procedure. Because the flow rate of an irrigation fluid through an irrigation lumen may be 2 milliliters, or 5 milliliters, or 13 milliliters, or 17 milliliters, or 30 milliliters or even up to 60 milliliters or more per minute at high pressure, in many embodiments, and it is important that irrigation lumen 8 allow for a clinically sufficient pressure and flow rate of an irrigation fluid, it is desirable to use a sealing means seal the juncture where electronic device assembly 66 extends through sideport 80 of first lumen section 74 (or the juncture where electronic device assembly 66 extends through sideport 80 of short assembly tube 102) such that any leakage of irrigation fluid from sideport 80 during use of ablation catheter 2 is minimized or desirably eliminated. This sealing of the juncture may be done using various sealing means as described below, all of which may be used alone or in any combination.

Figure 8:
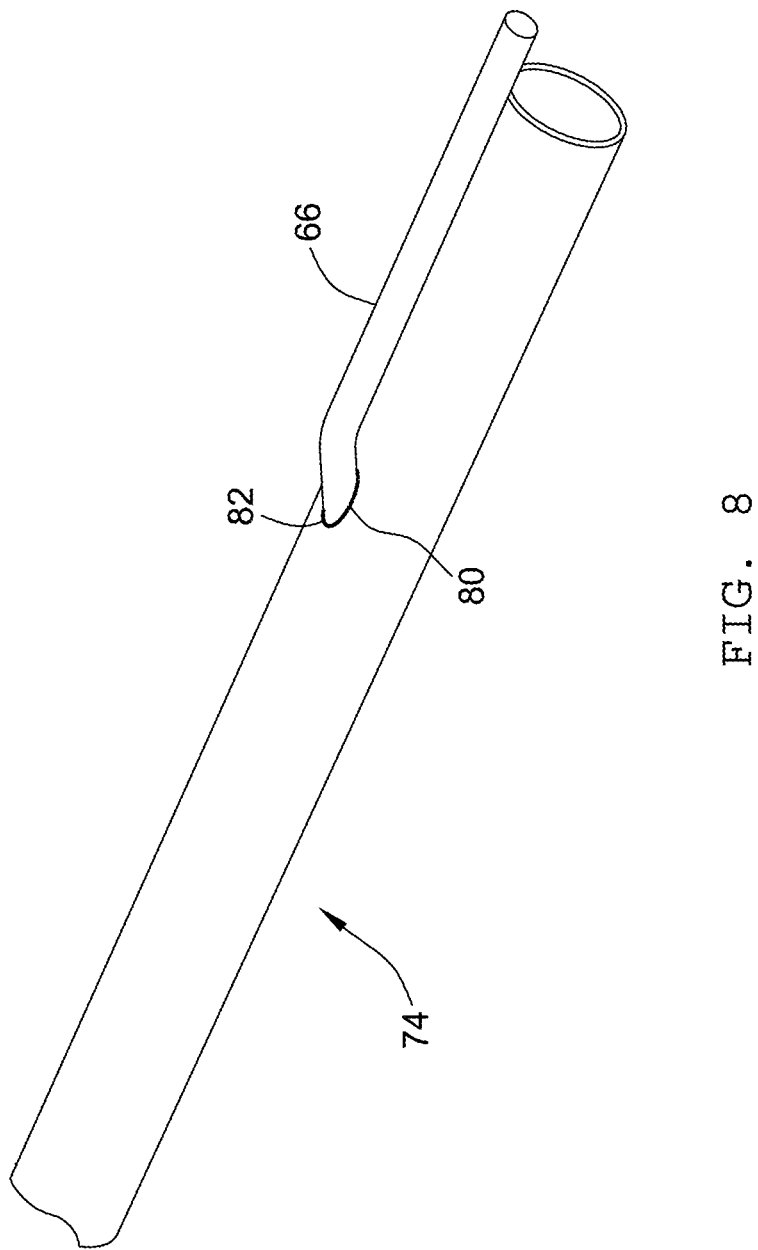
FIGS. 8-10 depict various embodiments for sealing a sideport in a lumen.

In one embodiment as illustrated in FIG. 8, the juncture where electronic device assembly 66 extends through sideport 80 of first lumen section 74 is sealed to minimize or eliminate leakage of irrigation fluid (not shown) from sideport 80 during an irrigated ablation procedure by introducing sealing compound 82 about the circumference of sideport 80. Sealing compound 82 seals the juncture where electronic device assembly 66 extends through sideport 80 of first lumen section 74 to make a water tight bond about the circumference of sideport 80. Sealing compound 82 may be applied to the juncture in a single layer, or may be applied two or more times to produce two or more layers of sealing compound 82. Desirably, sealing compound 82 forms a continuous bond line having a thickness of from about 0.0005 inches (about 0.0127 millimeters) to about 0.001 inches (about 0.0254 millimeters). Sealing compound 82 is suitably a flexible sealing compound that resists cracking upon the application of flex or torque. Sealing compound 82 may be comprised of any suitable adhesive or epoxy, including urethane-based adhesives and products, including Biothane 228 (Vertellus Performance Materials, Greensboro, N.C.).

Figure 9:
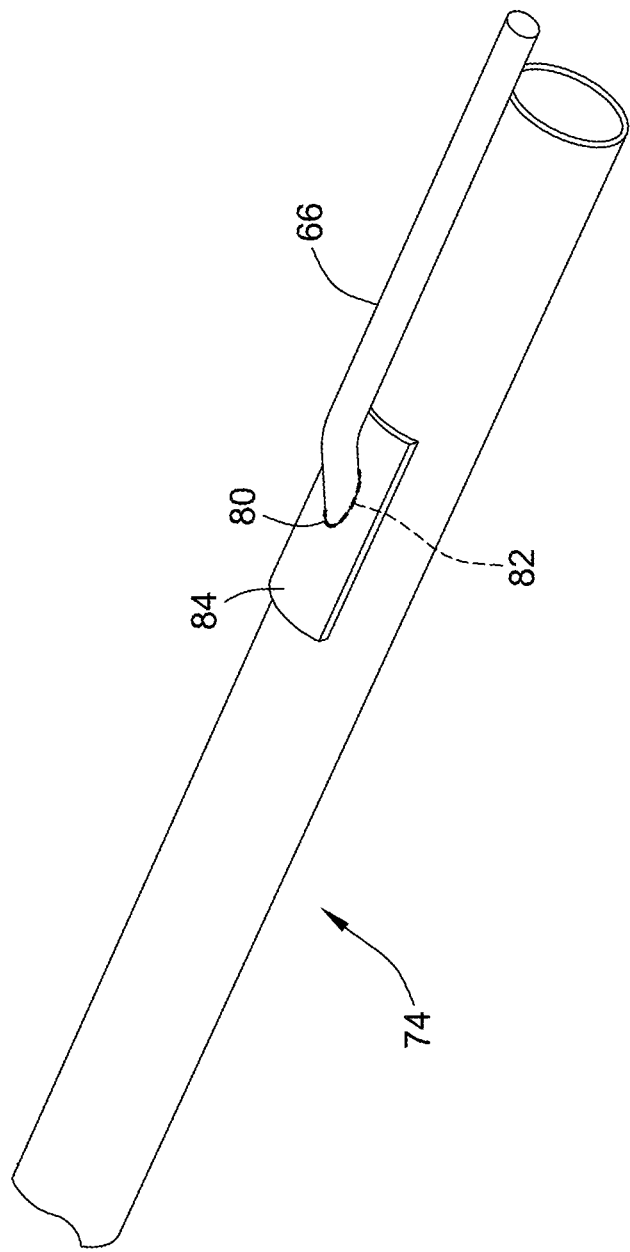

In another embodiment, sideport 80 of first lumen section 74 includes sealing compound 82 at the juncture where electronic device assembly 66 extends through sideport 80 of first lumen section 74 as shown in FIG. 8 and additionally includes sealing patch 84 as shown in FIG. 9 to further seal the juncture. In this embodiment, once the juncture is sealed with sealing compound 82 as described above, sealing patch 84 is introduced onto first lumen section 74 to cover the juncture. Alternatively, sealing patch 84 may be positioned prior to any sealing, with sealing done after positioning. Sealing patch 84 may be sized and configured to have an area of about 2 to about 5 times greater than the area of the juncture to be sealed, and may contain an opening sized generally slightly smaller (or about the same size) as the diameter of electronic device assembly 66 such that sealing patch 84 can be slid over electronic device assembly 66 and positioned around sideport 80 as shown in FIG. 9. Desirably, the opening in sealing patch 84 is located in about the middle of sealing patch 84. The length and width of sealing patch 84 may be selected to optimize the sealing capability of sealing patch 84 and each may be, in some embodiments, from about 3 millimeters to about 10 millimeters, including about 5 millimeters. Sealing patch 84 may be constructed of any material suitable for improving the sealing of the juncture where electronic device assembly 66 extends through sideport 80 of first lumen section 74, and may be the same or different material as first lumen section 74. In a desirable embodiment, sealing patch 84 is constructed of a polyimide-based material.

Once sealing patch 84 is positioned around sideport 80 on first lumen section 74, it is attached to first lumen section 74 using a suitable adhesive or epoxy as described above. In this embodiment, the juncture where electronic device assembly 66 extends through sideport 80 of first lumen section 74 is sealed with both sealing compound 82 and sealing patch 84 to provide improved sealing.

Figure 10:
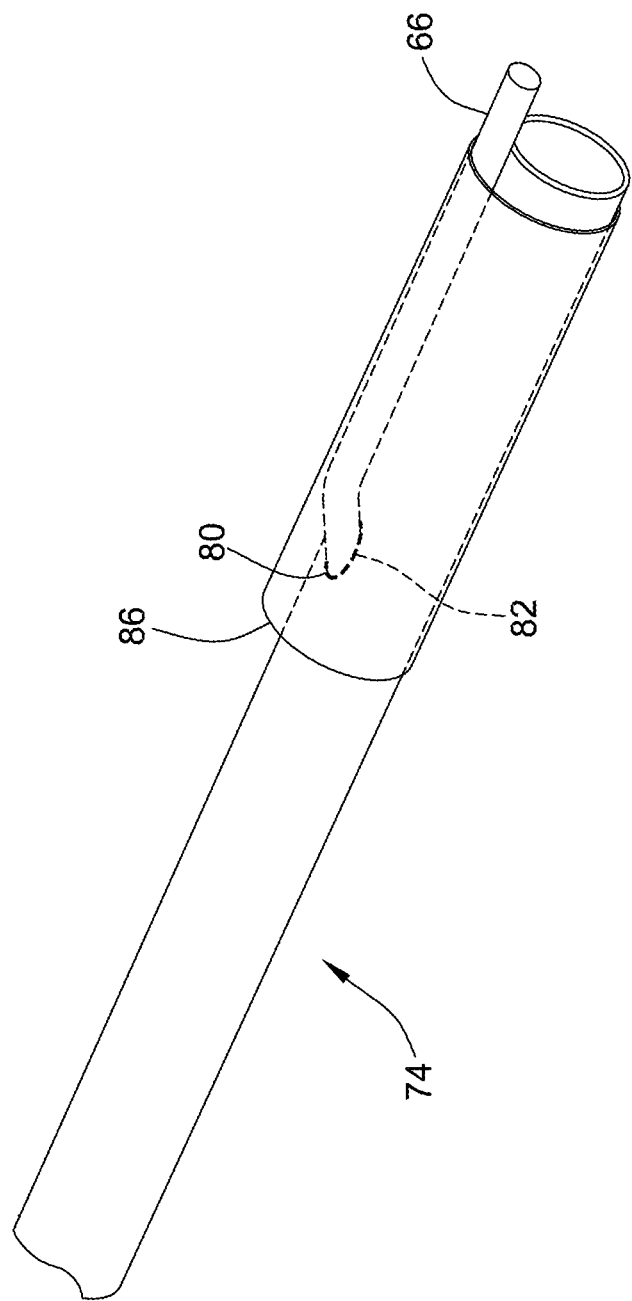

In another embodiment illustrated in FIG. 10, sideport 80 of first lumen section 74 includes sealing compound 82 at the juncture where electronic device assembly 66 extends through sideport 80 of first lumen section 74 as shown in FIG. 8, and additionally includes tubular sealing patch 86 as shown in FIG. 10 to further seal the juncture where electronic device assembly 66 extends through sideport 80 of first lumen section 74. In this embodiment, once the juncture is sealed with sealing compound 82 as described above, tubular sealing patch 86 is introduced onto first lumen section 74 to cover the juncture, as well as part of electronic device assembly 66 as shown in FIG. 10. Tubular sealing patch 86 is sized and configured such that it has a diameter slightly larger than the diameter of first lumen section 74 such that tubular sealing patch 86 can be slid over first lumen section 74 and electronic device assembly 66 and positioned where sideport 80 is about in the middle of tubular sealing patch 86 as shown in FIG. 10. Desirably, in some embodiments, tubular sealing patch 86 may have an outside diameter of about 0.047 inches (about 1.193 millimeters) and an inside diameter of about 0.045 inches (about 1.143 millimeters). The length of tubular sealing patch 86 may be selected to optimize the sealing capability of tubular sealing patch 86 and may be, in some embodiments, from about 3 millimeters to about 10 millimeters, including about 5 millimeters. Tubular sealing patch 86 may be constructed of any material suitable for improving the sealing of the juncture of sideport 80 and electronic device assembly 66, and may be the same or different material as first lumen section 74. In a desirable embodiment, sealing patch 84 is constructed of a polyimide-based material.

Once tubular sealing patch 86 is positioned around first lumen section 74 and electronic device assembly 66 with sideport 80 generally located in the middle of tubular sealing patch 86, tubular sealing patch 86 is attached to first lumen section 74 and electronic device assembly 66 using an adhesive or epoxy as described above. In this embodiment, the juncture where electronic device assembly 66 extends through sideport 80 of first lumen section 74 is sealed with both sealing compound 82 and tubular sealing patch 86. In other embodiments, the juncture where electronic device assembly 66 extends through sideport 80 of first lumen section 74 may be sealed with sealing compound 82, sealing patch 84, and tubular sealing patch 86.

In another embodiment of the present disclosure, electronic device assembly 66 extends out of first lumen section 74 such that sideport 80 in first lumen section 74 is not required. In this embodiment, there is no need to laser drill a hole (i.e., sideport 80) in first lumen section 74 as electronic device assembly 66 can exit first lumen section via an extension tube and as such, there is no risk of leakage of irrigation fluid at sideport 80. This "no sideport" embodiment for routing electronic device assembly 66 through first lumen section 74 utilizes a coupler as described below.

Figure 11:
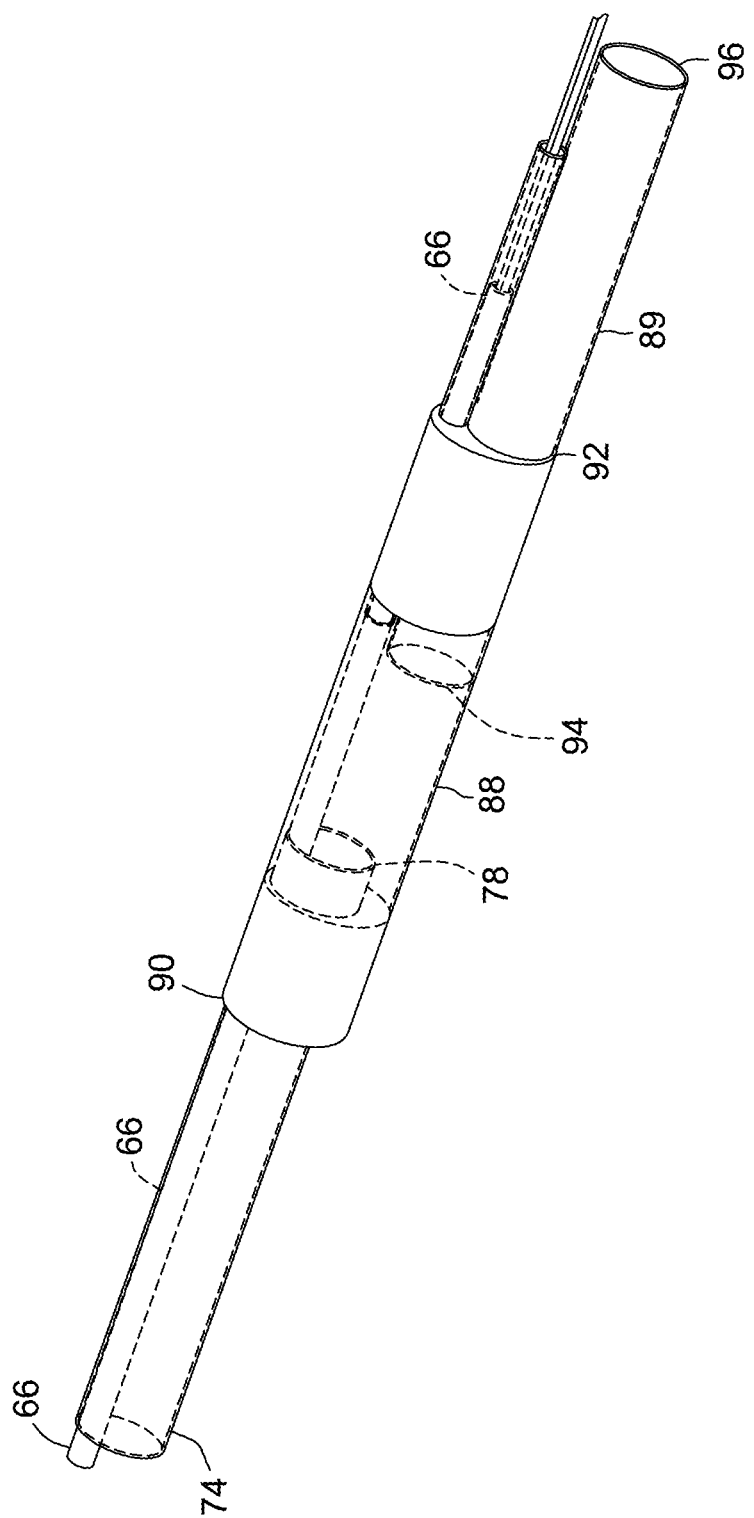
FIG. 11 depicts one embodiment of an electronic device assembly disposed within an irrigation lumen and extending out of the irrigation lumen without a sideport.

Referring now to FIG. 11, there is shown first lumen section 74 including electronic device assembly 66, coupler 88 having distal end 90 and proximal end 92, and extension tube 89 having distal end 94 and proximal end 96. Distal end 90 of coupler 88 is slid over proximal end 78 of first lumen section 74 such that electronic device assembly 66 extends through coupler 88 as illustrated in FIG. 11. Distal end 94 of extension tube 89 is slid into proximal end 92 of coupler 88 such that first lumen section 74 and extension tube 89 are in fluid communication through coupler 88. Extension tube 89 will generally have the same or similar outside diameter and inside diameter as first lumen section 74 described above. Coupler 88 is bonded to first lumen section 74 and extension tube 89 using a suitable adhesive as described herein. Coupler 88 has a suitable outside diameter to allow it to be slid into place as described above and in one example, may have an outside diameter of about 0.045 inches (about 1.143 millimeters).

Along with providing the benefit noted above of allowing electronic device assembly 66 to extend through first lumen section 74 without the need for a "hole" or sideport, coupler 88 may also provide increased articulation of the resulting structure, which may be beneficial for routing during manufacturing. Additionally, in other embodiments, coupler 88 may provide an advantageous location for an additional sideport to be introduced to allow access to first lumen section 74.

Once the juncture where electronic device assembly 66 extends through sideport 80 of first lumen section 74 has been sealed as desired, first lumen section 74 is utilized to complete manufacture of irrigation lumen 8 for use in ablation catheter 2. (Although the manufacture of irrigation lumen 8 is described herein utilizing first lumen section 74 including sideport 80, it should be recognized that the manufacturing processes described herein are equally applicable to embodiments where first lumen section 74 does not include sideport 80 but instead includes coupler 88 as described above.)

Figure 12:
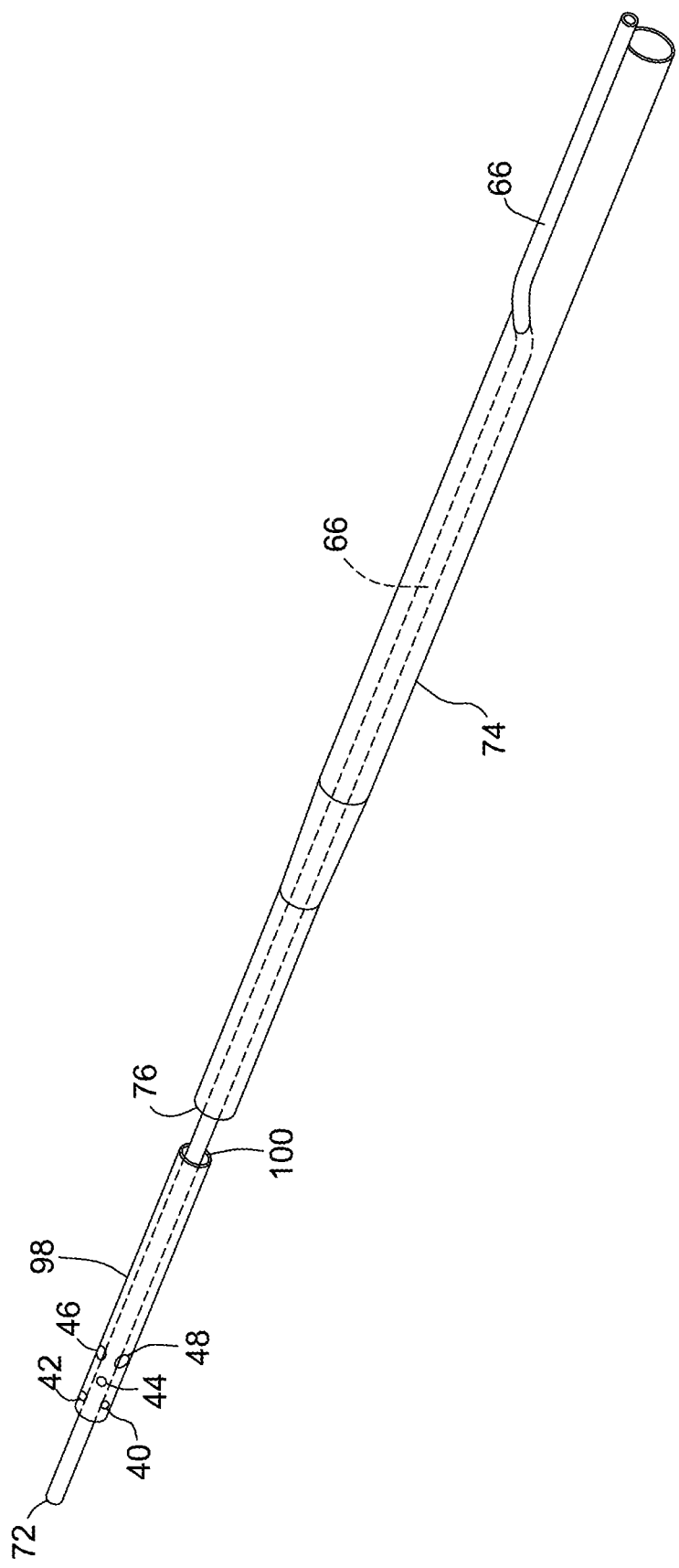
FIGS. 12-14 depict various embodiments for constructing an irrigation lumen.
Figure 13:
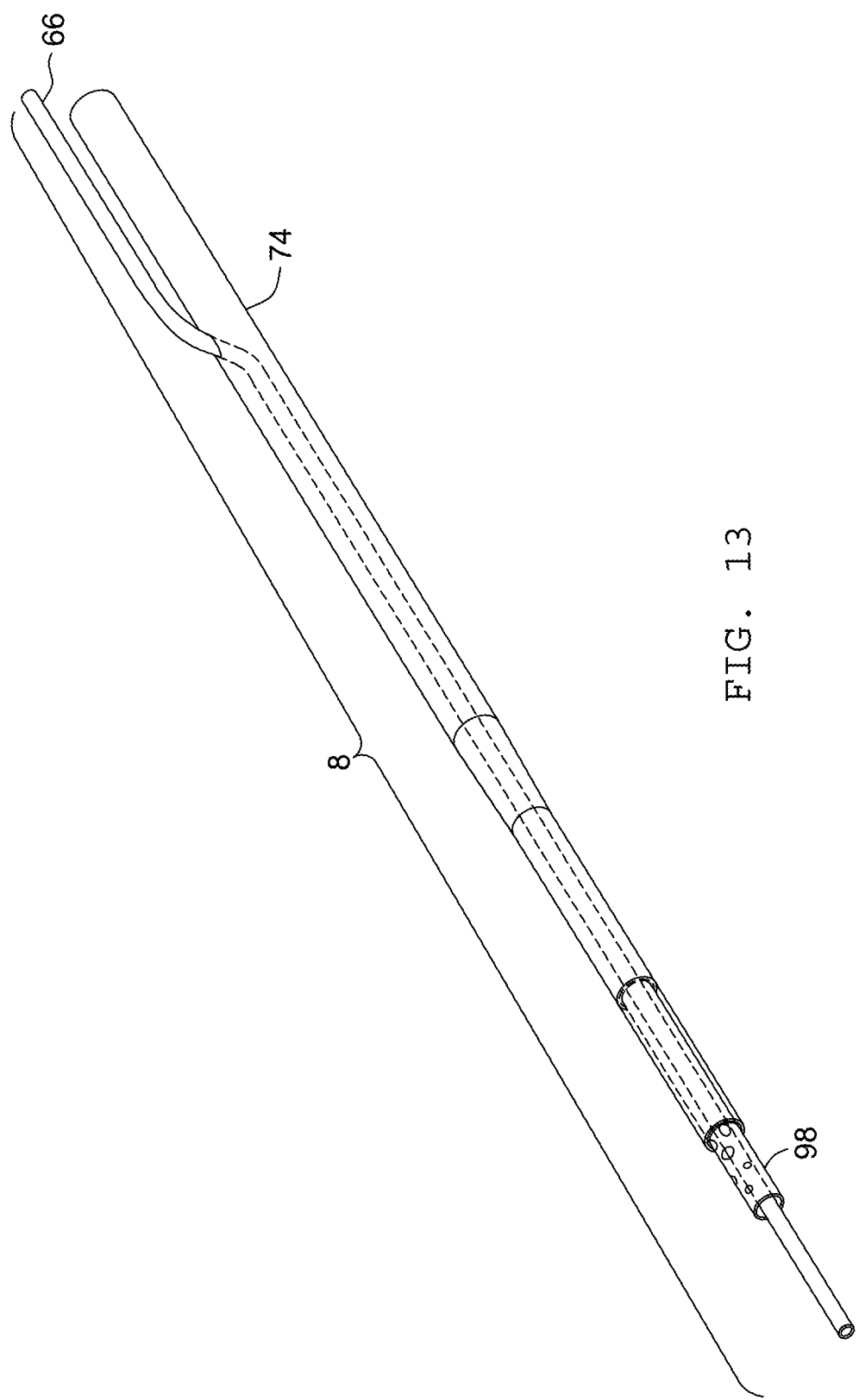

Referring now to FIG. 12, there is shown first lumen section 74 having distal end 76, electronic device assembly 66 having distal end 72, and second lumen section 98 having proximal end 100. Second lumen section 98 includes holes 40, 42, 44, 46, and 48 for dispersing an irrigation fluid (not shown). Second lumen section 98 may be constructed of the same material as first lumen section 74, or may be constructed of another material. Desirably, second lumen section 98 is constructed from a polyimide material. To connect second lumen section 98 to first lumen section 74, an adhesive or epoxy as described herein (not shown) is applied to second lumen section 98 (being careful not to introduce adhesive into any of holes 40, 42, 44, 46, or 48) and proximal end 100 of second lumen section 98 is slid into distal end 76 of electronic device assembly 66. FIG. 13 shows second lumen section 98 positioned within first lumen section 74 to form irrigation lumen 8. In some embodiments, second lumen section 98 may have an outside diameter of about 0.023 inches (about 0.5842 millimeters) and in inside diameter of about 0.021 inches (about 0.5334 millimeters).

Figure 14:
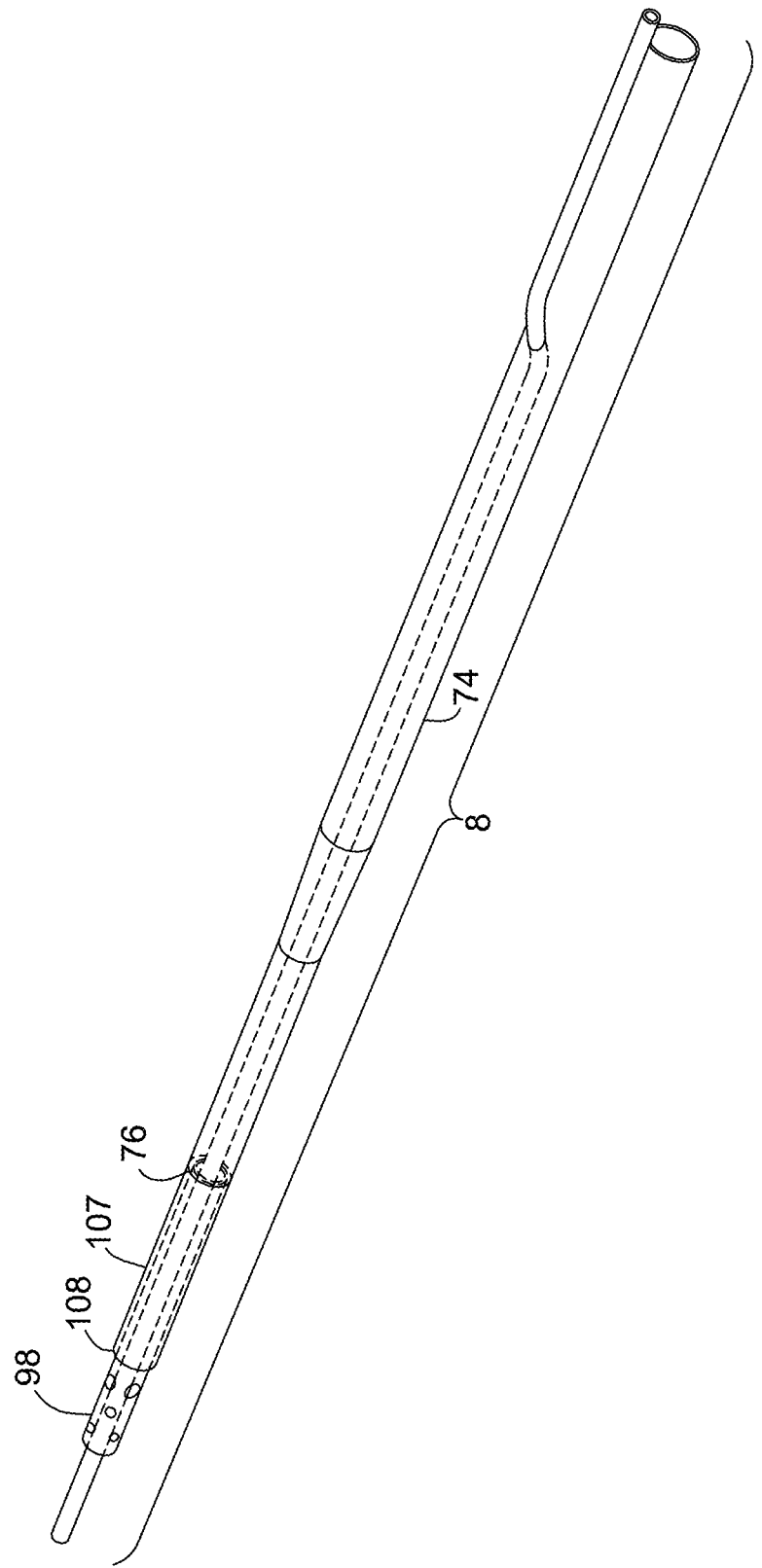

In an alternative embodiment, shown in FIG. 14, irrigation lumen 8 may be constructed as follows incorporating third lumen section 107 into irrigation lumen 8. Second lumen section 98 as described above is inserted into distal end 108 of third lumen section 107 prior to the joined combination of second lumen section 98 and third lumen section 107 being inserted into distal end 76 of first lumen section 74. In this embodiment, third lumen section 107 acts to evenly distribute an irrigation fluid (not shown) into second lumen section 98. In this alternative embodiment, it is generally desirable for third lumen section 107 to have length of from about 1 millimeter to about 3 millimeters, or even about 2.5 millimeters after insertion in the third lumen section 107. In some embodiments, third lumen section 107 may have an outside diameter of about 0.0305 inches (about 0.7747 millimeters) and an inside diameter of about 0.0265 inches (about 0.6731 millimeters).

Figure 15:
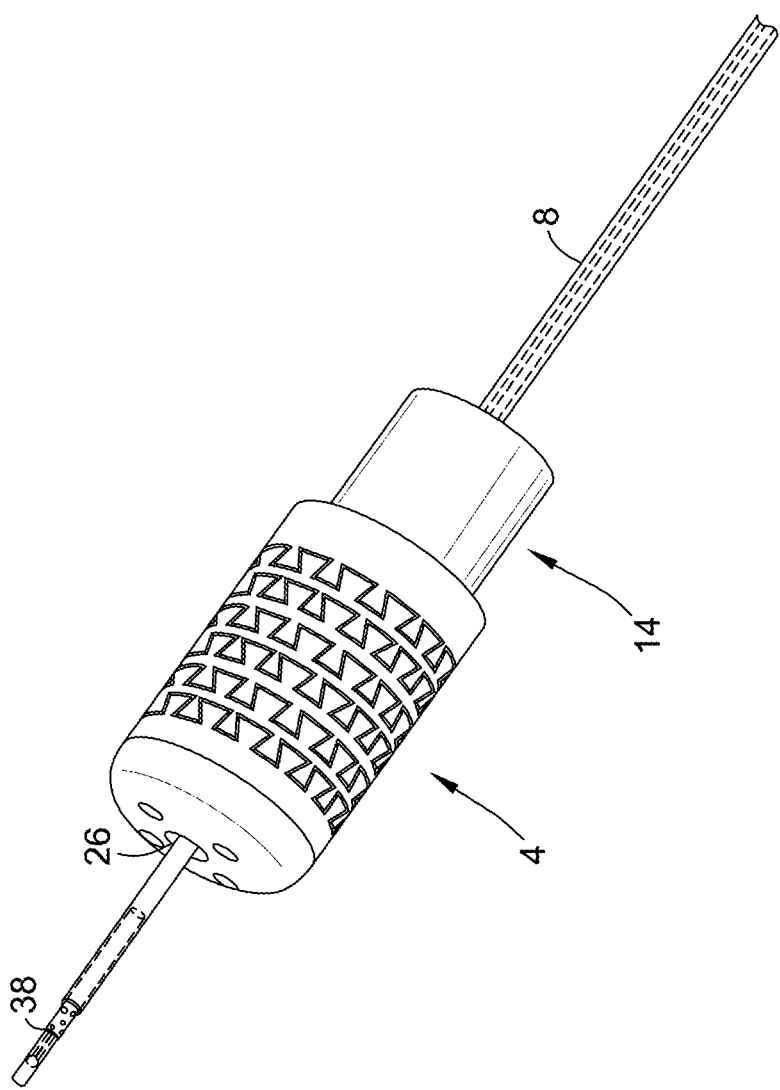
FIGS. 15-17 depict the positioning of an irrigation lumen in an electrode tip assembly, with FIG. 16 having portions cut away to show internal construction.
Figure 16:
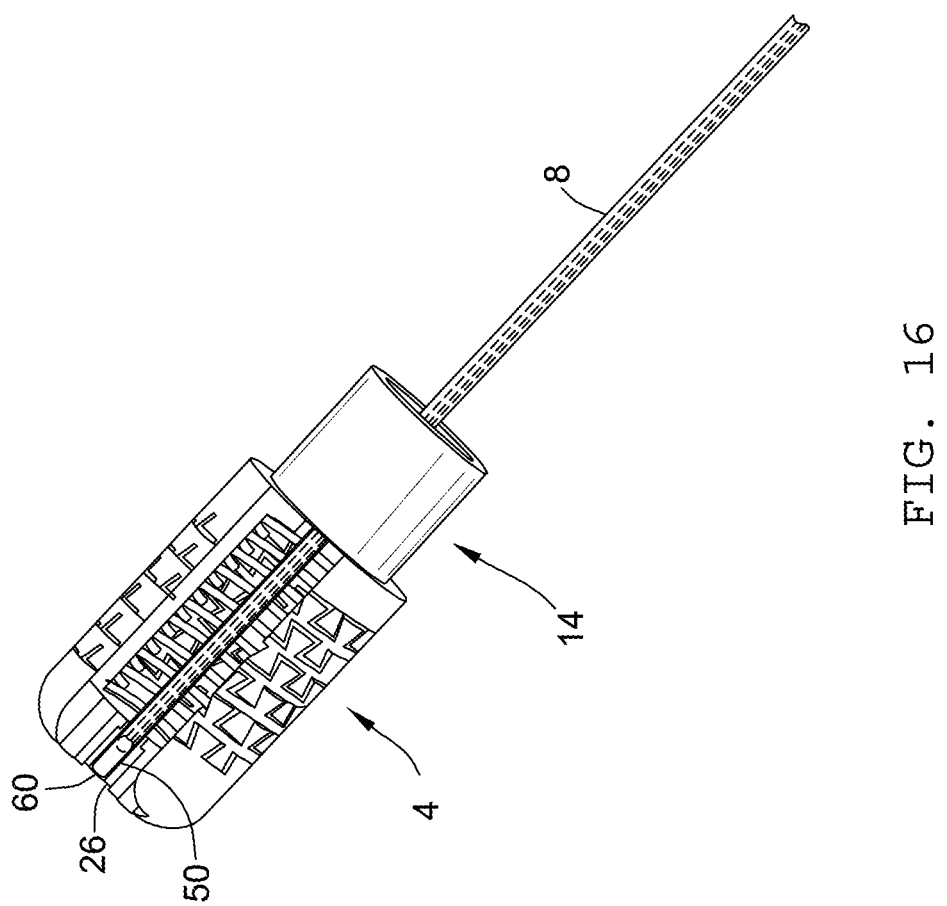

Once irrigation lumen 8 is constructed as described above, it may be positioned within electrode tip assembly 4. For this positioning, as shown in FIG. 15, distal end 38 of irrigation lumen 8 is introduced into stem 14 of electrode tip assembly 4 and urged through electrode tip assembly 4 until distal end 38 of irrigation lumen 8 is pushed out of counterbore 26 of electrode tip assembly 4. Once distal end 38 of irrigation lumen 8 has been urged through counterbore 26, distal end 38 is pulled back into counterbore 26 until distal end 60 of insulating element 50 is flush with the counterbore 26 as shown in FIG. 16. Although described and illustrated in FIG. 16 as flush with counterbore 26, it should be understood that distal end 60 of insulating element 50 could be positioned at any place within counterbore 26 as desired.

Figure 17:
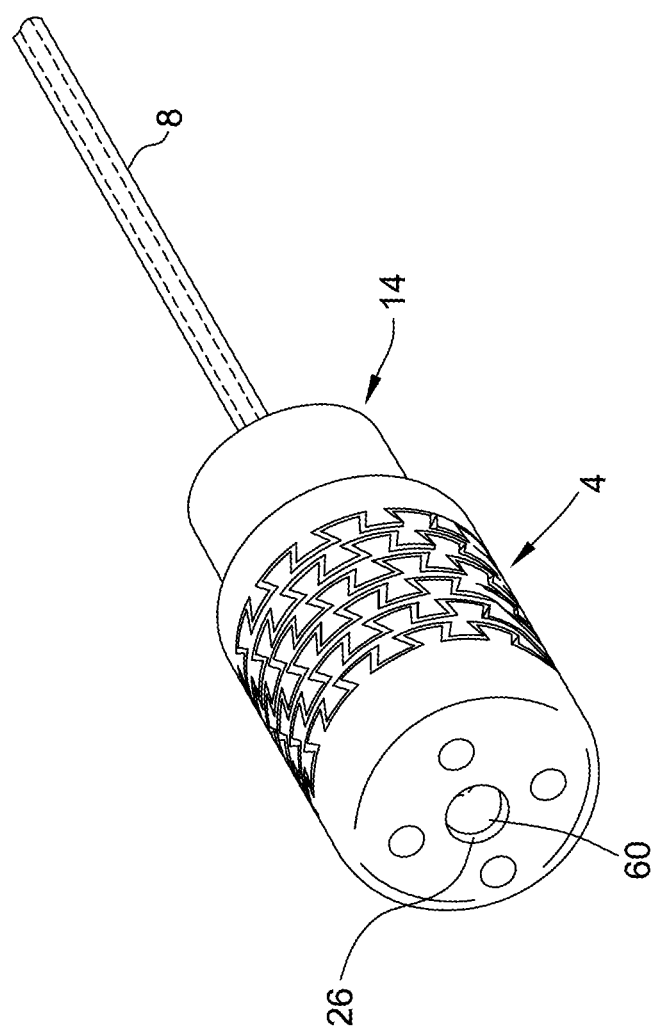

Once distal end 60 of insulating element 50 is properly positioned within counterbore 26 of electrode tip assembly 4, counterbore 26 is filled with adhesive (not shown) to stabilize distal end 60 of insulating element 50 in counterbore 26 as shown in FIG. 17. Desirably, the adhesive is a thermally conductive adhesive.

Figure 18:
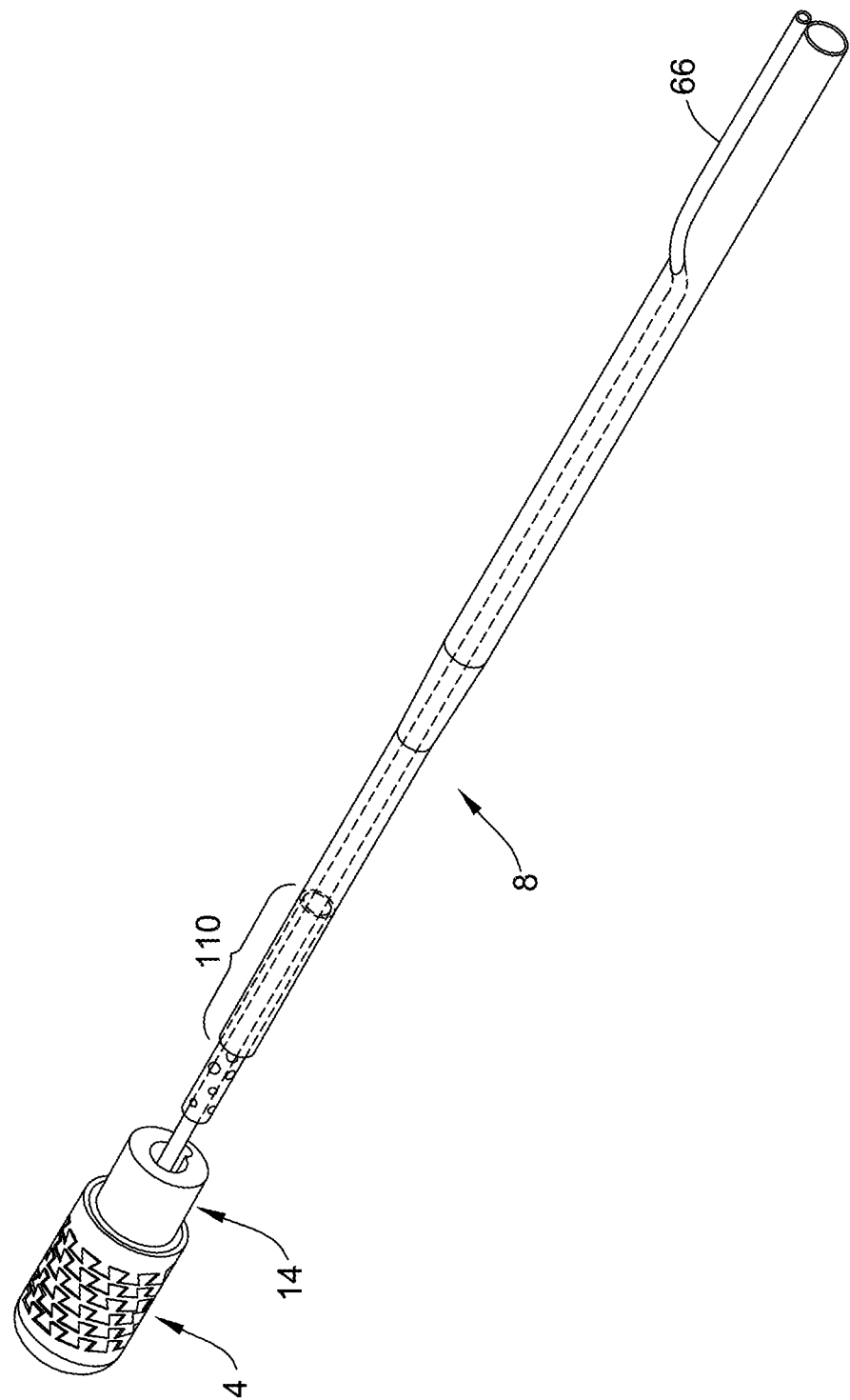
FIGS. 18-19 depict the construction of an ablation catheter of the present disclosure.
Figure 19:
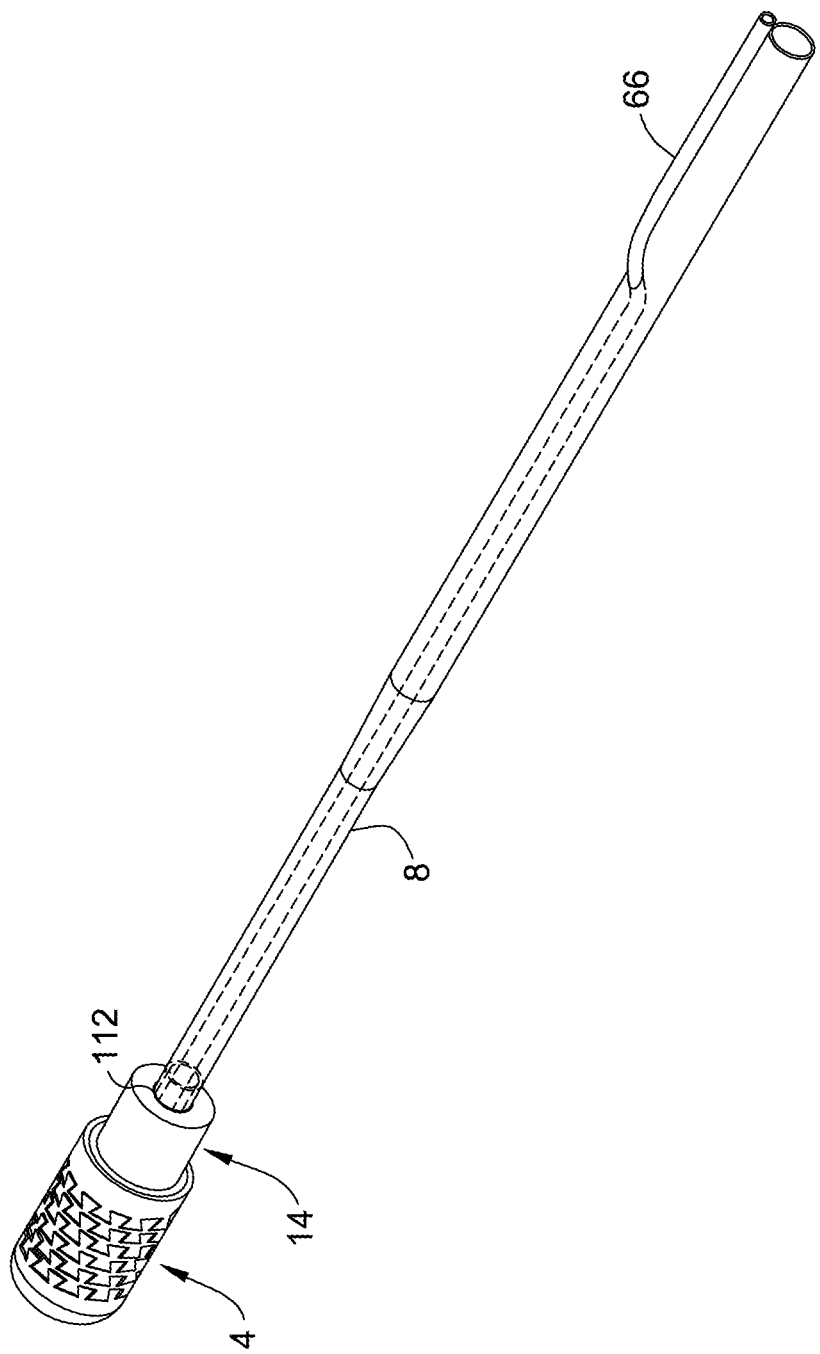

After distal end 60 of insulating element 50 has been stabilized in counterbore 26 by the adhesive and the adhesive has dried, irrigation lumen 8 is positioned and attached to electrode tip assembly 4 in stem 14 as shown in FIGS. 18 and 19. An adhesive as described above (not shown) is applied to an upper section 110 of irrigation lumen 8 and, while electronic device assembly 66 is held to keep it tight, irrigation lumen 8 is inserted into stem 14 of electrode tip assembly 4 and the adhesive is allowed to dry. To further seal irrigation lumen 8 within electrode tip assembly 4 and provide additional protection against leakage of an irrigation fluid (not shown), a bead of adhesive 112 is introduced at the juncture of stem 14 and irrigation lumen 8.

As noted above, the present disclosure contemplates numerous alternative embodiments where one, two, three or more electronic devices are present in the electrode tip assembly as described herein. One or more electronic devices may be disposed inside of a lumen, and one or more electronic devices may be disposed outside of a lumen. In one specific alternative embodiment of the present disclosure, there is provided an ablation catheter including an electrode tip assembly including a first electronic device disposed in an irrigation lumen and a second electronic device disposed outside of the irrigation lumen and located at least partially in the stem of the electrode tip assembly.

Figure 20:
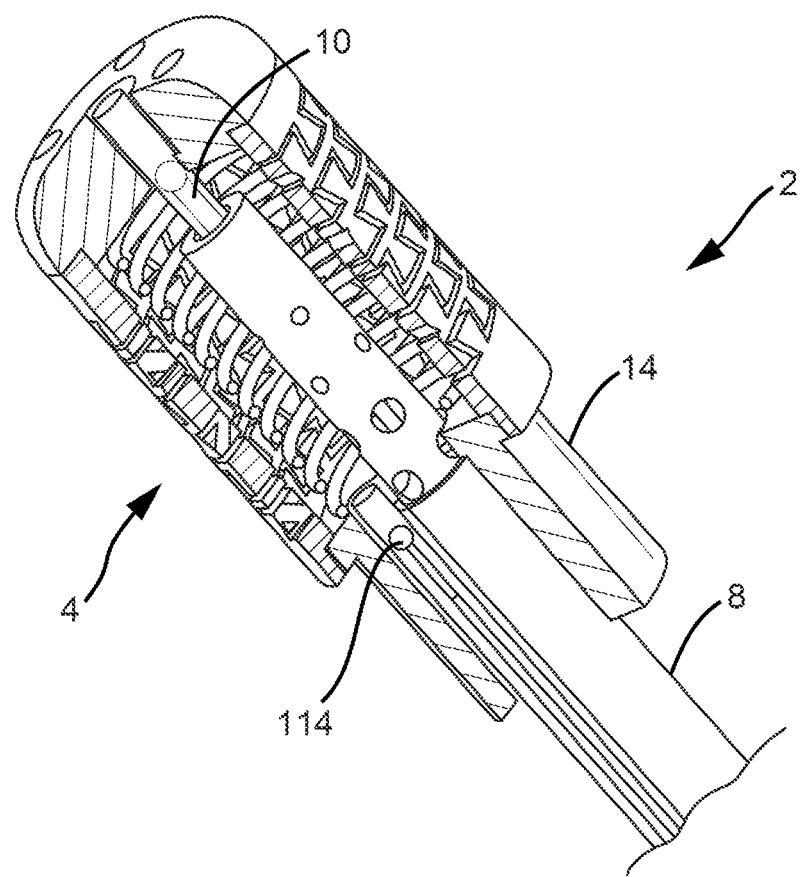
FIG. 20 depicts one embodiment of an ablation catheter of the present disclosure with portions cut away to reveal internal construction.

Turning now to FIG. 20, this alternative embodiment is illustrated and there is shown ablation catheter 2 including electrode tip assembly 4, stem 14, irrigation lumen 8, electronic device 10 and second electronic device 114. Electronic device 10 is positioned at least partially in irrigation lumen 8 and is constructed as described above. Second electronic device 114 is positioned at least partially in stem 14, but outside of irrigation lumen 8. In this exemplary alternative embodiment where two separate electronic devices are present, electronic device 10 disposed in irrigation lumen 8 could be a GPS sensor, and second electronic device 114 located outside of irrigation lumen 8 could be a thermocouple. Of course, each of the two electronic devices could be any other electronic device as described herein. In another exemplary embodiment, a first electronic device includes a thermocouple positioned at least partially within an irrigation lumen and a second electronic device also includes a thermocouple positioned in the stem of the electrode tip assembly such that a relative difference in temperature between the first thermocouple and the second thermocouple can be calculated and/or utilized during a procedure.

Although a number embodiments of this disclosure have been described above with a certain degree of particularity, those skilled in the art could make numerous alterations to the disclosed embodiments without departing from the spirit or scope of the disclosure. For example, a notable feature of this disclosure is the presence of an electronic device in a lumen, such as an irrigation lumen. One skilled in the art may change the materials used to construct the lumen, the diameters of the materials, etc. without departing from the spirit or scope of the disclosure. It is intended that all matter contained in the above description or shown in the accompanying drawings shall be interpreted as illustrative only and not limiting. Changes in detail or structure may be made without departing from the spirit of the disclosure as defined in the claims.

Any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated by reference herein. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Example

The following example illustrates specific features of the ablation catheters of the present disclosure. The example is given solely for the purpose of illustration and is not to be construed as a limitation of the present disclosure, as many variations thereof are possible without departing from the spirit and scope of the disclosure.

In this Example, the amount of flow rate, pressure, and leakage of a liquid (water) was evaluated for five different irrigation lumen designs (Designs 1-5), each of which incorporated a thermocouple (similar to electronic device 10 of FIG. 2) within the irrigation lumen. Each design, along with a design replicate, consisted of a flexible electrode tip assembly (similar to electrode tip assembly 4 of FIG. 2), a tapered irrigation lumen, polyimide tubing as described, and a thermocouple electronic device. Each design evaluated differed in the process used to insert the thermocouple into the irrigation lumen and seal any sideport present. Designs 1-5 are detailed below.

Design 1

Design 1 was constructed by inserting a thermocouple through a predrilled sideport (diameter of about 0.0125 inches (about 0.3175 millimeters)) located about 51.25 inches from the distal end of a tapered polyimide irrigation lumen. The thermocouple was introduced into the sideport and threaded through the length of the irrigation lumen. The sideport was sealed with a urethane-based adhesive completely around the juncture of the thermocouple and the irrigation lumen (similar to that shown in FIG. 8).

Design 2

Design 2 was constructed by first forming a polyimide patch out of a polyimide material and drilling a hole (diameter of about 0.0125 inches (about 0.3175 millimeters)) in the center of the polyimide patch such that the thermocouple could be pushed through the hole. The polyimide patch was bonded to the irrigation lumen (same dimensions as that in Design 1) such that the hole in the polyimide patch aligned with a predrilled sideport in the irrigation lumen. A thermocouple was then inserted through the polyimide patch and irrigation lumen. A urethane-based adhesive was then applied about the entire juncture of the hole through which the thermocouple was placed and the juncture of the patch and the irrigation lumen (similar to that shown in FIG. 9).

Design 3

Design 3 was constructed by inserting a thermocouple through a predrilled sideport in an irrigation lumen (same dimensions as that in Design 1), and by further sliding a polyimide tube (about 5 millimeters long) with a larger diameter than the irrigation lumen over the sideport and the thermocouple creating a tubular over-patch (similar to that shown in FIG. 10). The tubular over-patch acted as a sleeve to cover the area that could potentially be exposed to leakage. A urethane-based adhesive was then applied around the juncture of the sideport and the irrigation lumen and to the over-patch and irrigation lumen to bond and seal the sideport and tubular over patch.

Design 4

Design 4 was constructed using a polyimide tube (coupler) having a slightly larger outer diameter than the outer diameter of the irrigation lumen (same dimensions as that in Design 1) to couple together a first and second section of the irrigation lumen such that the thermocouple could exit the irrigation lumen without the need for a sideport (similar to that shown in FIG. 11). Specifically, the irrigation lumen was cut at the same location that the sideport would be drilled in Designs 1-3 described above. The thermocouple was then fed through one end of the larger diameter coupler and into the irrigation lumen. Both ends of the coupler were sealed and bonded to their respective irrigation lumen piece using a urethane-based adhesive. This design allowed the thermocouple to be inserted straight into the irrigation lumen as opposed being pushed through a sideport as in Designs 1-3.

Design 5

Design 5 was constructed by inserting a thermocouple through a predrilled sideport (same dimensions as in Design 1) in a short polyamide tube (about 12 millimeters long) having a diameter slightly larger than the irrigation lumen (same dimensions as that in Design 1), and sliding the polyamide tube over the irrigation lumen to create an overlap. Once the thermocouple was pulled out to the correct length and fed into the irrigation lumen, ends of the polyamide tube and the irrigation lumen were bonded together (with one overlap of about 3 millimeters) using a urethane-based adhesive (similar to that shown in FIG. 7). The adhesive was also applied around the circumference of the sideport in the polyamide tube similar to that described in Design 1. This design takes into account the ease of assembly by using a polyimide tube that can be slid over the main lumen. The use of a shortened polyimide tube in combination with the irrigation lumen made the assembly process faster and easier since the assembler only had to push the thermocouple a short distance due to the shorter length of the polyimide tube.

Test Procedure for Evaluating Flow Rate, Pressure, and Amount of Leakage

The end of a conventional irrigation solution tube connected to a solution pump was inserted into a large beaker willed with water. A conventional pressure sensor was attached to the end of the irrigation solution tube, and one of Designs 1-5 as described above was attached to the other end of the irrigation solution tube. The irrigation solution tube was cleared of bubbles by setting the flow rate to 60 ml/min and running the water into an empty beaker until the flow was steady and no bubbles were visible. A clean and empty beaker was weighed and the scale was zeroed. The flow rate was set to the desired test amount (2 ml/min, 13 ml/min, 17 ml/min, 30 ml/min, or 60 ml/min), and a dry paper towel was placed under the section where the thermocouple enters the irrigation lumen in the Design to be tested. The distal end of the Design to be tested was held over the beaker that was weighed, and the pump and a timer were started simultaneously.

The peak pressure was recorded, and the paper towel was observed for any dark spots indicating leakage from the Design being tested. After a time period of one minute, the pump was disengaged and the test sample was immediately removed from the beaker. The contents of the beaker were weighed on the zeroed scale and the data was recorded.

The inside of the beaker was wiped until clean and the scale was re-zeroed with the beaker on it. The process was repeated for each of the Designs to be tested, as well as for their replicates.

Results and Discussion

This series of tests evaluated each Design at five different flow rates. Table 1 below shows the averages for a given flow rate. None of the Designs exhibited any leaks (Pressures given in psi).

TABLE 1

| | Average | | | | | | | | | |
|---|---|---|---|---|---|---|---|---|---|---|
| | 2 ml/min | | 13 ml/min | | 17 ml/min | | 30 ml/min | | 60 ml/min | |
| Design | Output | Pressure | Output | Pressure | Output | Pressure | Output | Pressure | Output | Pressure |
| 1A | 2.05 | 1.9 | 13.26 | 11.6 | 17.38 | 15.5 | 30.18 | 28.1 | 61.69 | 66.6 |
| 1B | 2.07 | 2.4 | 13.28 | 14.2 | 17.21 | 18.3 | 30.33 | 32.6 | 60.1 | 76.6 |
| 2A | 2.07 | 2.4 | 13.26 | 14.2 | 17.35 | 18.2 | 30.33 | 32.2 | 60.57 | 75.5 |
| 2B | 2.14 | 2.2 | 13.61 | 14.5 | 17.76 | 18.9 | 30.88 | 34.5 | Occl | Occl |
| 3A | 2.06 | 2.2 | 13.23 | 12.7 | 17.21 | 16.8 | 30.25 | 29.9 | 60.12 | 72.2 |
| 3B | 2.08 | 2.1 | 13.27 | 12.4 | 17.16 | 15.9 | 29.99 | 27.6 | 60.18 | 68.2 |
| 4A | 2.08 | 2.3 | 13.32 | 14.7 | 17.26 | 18.8 | 30.39 | 33 | 60.05 | 76.4 |
| 4B | 2.06 | 2.4 | 13.24 | 13.7 | 17.16 | 17.8 | 30.27 | 32.1 | 60.15 | 76.8 |
| 5A | 1.99 | 2.3 | 12.98 | 14.4 | 17.1 | 18.3 | 29.89 | 31.3 | 60.31 | 75.7 |

TABLE 1-continued

| | Average | | | | | | | | | |
|---|---|---|---|---|---|---|---|---|---|---|
| | 2 ml/min | | 13 ml/min | | 17 ml/min | | 30 ml/min | | 60 ml/min | |
| Design | Output | Pressure | Output | Pressure | Output | Pressure | Output | Pressure | Output | Pressure |
| 5B | 2.07 | 2.4 | 13.27 | 14.3 | 17.02 | 18 | 30.34 | 31.2 | 59.91 | 73.7 |
| Average | 2.07 | 2.25 | 13.27 | 13.67 | 17.26 | 17.63 | 30.29 | 31.24 | 60.34 | 73.53 |

Table 1.
Pressure and flow averages.
Value labeled as "Occl" indicate an occlusion which is due to high pressure.

The average output for each Design tested was within the acceptance criteria of within ±10% of the designated flow rate, and the biggest difference when compared to a conventional irrigation lumen without a thermocouple positioned therein was the increase in the pressure. Specifically, due to a decrease in cross sectional area (free space) of the irrigation lumen caused by the thermocouple being positioned in the irrigation lumen, the pressure increased as flow rate increased. The test samples showed a 1:1 ratio in flow rate vs. pressure. The only occlusion detected by the pump was in the Design 2 replicate. Specifically, at 60*ml/min the pressure rose and set off the occlusion alarm.*

Based on the results obtained in this Example, it can be concluded that the volumetric flow output was not significantly impacted by the addition of the thermocouple into the lumen, as sufficient flow rates and acceptable pressure could be maintained without leakage. Additionally, since none of the Designs showed any indications of leakage upon use, it can be concluded that irrigation lumens including an electronic device disposed therein (such as the thermocouple) can be constructed to be leak-free.

The invention claimed is:

1. An irrigated ablation catheter comprising:
   an electrode tip assembly;
   an irrigation lumen comprising a tubular structure configured to contact and carry irrigation fluid and having a distal end and a proximal end;
   a thermocouple device contained within an insulating element and having a distal end and a proximal end and being disposed at least partially within the irrigation lumen, the insulating element containing the thermocouple device being in contact with the irrigation fluid when disposed within the irrigation lumen, the proximal end of the thermocouple device extending out of the irrigation lumen near the proximal end of the irrigation lumen; and
   wherein the irrigation lumen additionally includes at least one sideport, wherein the at least one sideport includes a sealing means for sealing the at least one sideport, and wherein the sealing means includes an adhesive bead about a circumference of the at least one sideport.

2. The irrigated ablation catheter of claim 1 wherein the distal end of the irrigation lumen is at least partially disposed in the electrode tip assembly.

3. The irrigated ablation catheter of claim 1 wherein the distal end of the thermocouple device extends past the distal end of the irrigation lumen and into the electrode tip assembly.

4. The irrigated ablation catheter of claim 1 wherein the proximal end of the thermocouple device extends through the at least one sideport on the irrigation lumen.

5. The irrigated ablation catheter of claim 1 wherein the sealing means additionally includes a sealing patch sized and configured for adhesively attaching about the circumference of the at least one sideport.

6. The irrigated ablation catheter of claim 1 wherein the sealing means additionally includes a tubular sealing patch sized and configured for adhesively attaching about the circumference of the at least one sideport.

7. The irrigated ablation catheter of claim 1 wherein the irrigation lumen including the thermocouple device disposed at least partially therein is connected by a coupler to an extension tube, wherein the proximal end of the thermocouple device extends through the coupler and into the extension tube.

8. The irrigated ablation catheter of claim 1 further comprising an electronic device selected from the group consisting of a global positioning system sensor, a pressure sensor, a lab-on-a-chip device, a transducer, and combinations thereof, wherein the electronic device is disposed at least partially within the irrigation lumen, the proximal end of the electronic device extending out of the irrigation lumen near the proximal end of the irrigation lumen.

9. The irrigated ablation catheter of claim 1 wherein the irrigation lumen is comprised of two or more pieces bonded together.

10. The irrigated ablation catheter of claim 1 wherein the electrode tip assembly is a flexible electrode tip assembly.

* * * * *